United States Patent
Rusch et al.

(10) Patent No.: US 10,242,437 B2
(45) Date of Patent: Mar. 26, 2019

(54) SYSTEMS AND METHODS FOR DETECTING SYRINGE SEAL DEFECTS

(71) Applicant: W. L. Gore & Associates, Inc., Newark, DE (US)

(72) Inventors: Greg Rusch, Newark, DE (US); Kevin N. Murphy, Baltimore, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 26 days.

(21) Appl. No.: 15/404,967

(22) Filed: Jan. 12, 2017

(65) Prior Publication Data

US 2017/0206647 A1   Jul. 20, 2017

Related U.S. Application Data

(60) Provisional application No. 62/279,009, filed on Jan. 15, 2016.

(51) Int. Cl.

| | |
|---|---|
| *G06T 7/00* | (2017.01) |
| *A61M 5/31* | (2006.01) |
| *G01M 3/38* | (2006.01) |
| *G01M 13/005* | (2019.01) |
| *G01N 21/90* | (2006.01) |
| *G06T 7/90* | (2017.01) |
| *A61M 5/315* | (2006.01) |
| *G01N 21/952* | (2006.01) |

(52) U.S. Cl.
CPC ......... *G06T 7/0004* (2013.01); *A61M 5/3129* (2013.01); *A61M 5/31513* (2013.01); *G01M 3/38* (2013.01); *G01M 13/005* (2013.01); *G01N 21/90* (2013.01); *G01N 21/9054* (2013.01); *G06T 7/90* (2017.01); *A61M 2005/3131* (2013.01); *G01N 21/952* (2013.01); *G06T 2207/10004* (2013.01)

(58) Field of Classification Search
CPC ............... G06T 7/0004; G06T 7/90; G06T 2207/10004
See application file for complete search history.

(56) References Cited

U.S. PATENT DOCUMENTS

| | | |
|---|---|---|
| 5,374,473 A | 12/1994 | Knox et al. |
| 5,708,044 A | 1/1998 | Branca |
| 5,792,525 A | 8/1998 | Fuhr et al. |
| 6,030,694 A | 2/2000 | Dolan et al. |
| 6,541,589 B1 | 4/2003 | Baillie |
| 7,521,010 B2 | 4/2009 | Kennedy et al. |

(Continued)

FOREIGN PATENT DOCUMENTS

| | | |
|---|---|---|
| EP | 0683388 A1 * | 5/1995 |
| EP | 0683388 | 11/1995 |

(Continued)

OTHER PUBLICATIONS

International Search Report PCT/US2017/013294 dated Mar. 30, 2017.

*Primary Examiner* — Ping Y Hsieh
(74) *Attorney, Agent, or Firm* — Amy Miller

(57) ABSTRACT

Systems and methods for detecting syringe seal defects are described, including associated syringe stopper designs having seal areas and indicating areas, as well as associated inspection systems and methods for optical imaging and analysis for syringe seal defects in dry and wet syringes.

9 Claims, 7 Drawing Sheets

(56) References Cited

U.S. PATENT DOCUMENTS

| | | | |
|---|---|---|---|
| 7,531,611 B2 | 5/2009 | Sabol et al. | |
| 8,637,144 B2 | 1/2014 | Ford | |
| 8,658,707 B2 | 2/2014 | Xu et al. | |
| 9,139,669 B2 | 9/2015 | Xu et al. | |
| 2008/0001104 A1* | 1/2008 | Voigt | G01N 21/8851 |
| | | | 250/559.46 |
| 2011/0083489 A1 | 4/2011 | Glunz et al. | |
| 2013/0343620 A1* | 12/2013 | Okuda | G06T 7/0012 |
| | | | 382/128 |
| 2015/0293031 A1* | 10/2015 | Fisk | C23C 16/04 |
| | | | 356/51 |

FOREIGN PATENT DOCUMENTS

| | | |
|---|---|---|
| EP | 1785692 | 5/2007 |
| EP | 2371406 | 10/2011 |
| EP | 2381246 | 10/2011 |
| EP | 2851677 | 3/2015 |
| JP | H07 311156 | 11/1995 |
| JP | H1123488 | 1/1999 |
| JP | 2013 252177 | 12/2013 |

* cited by examiner

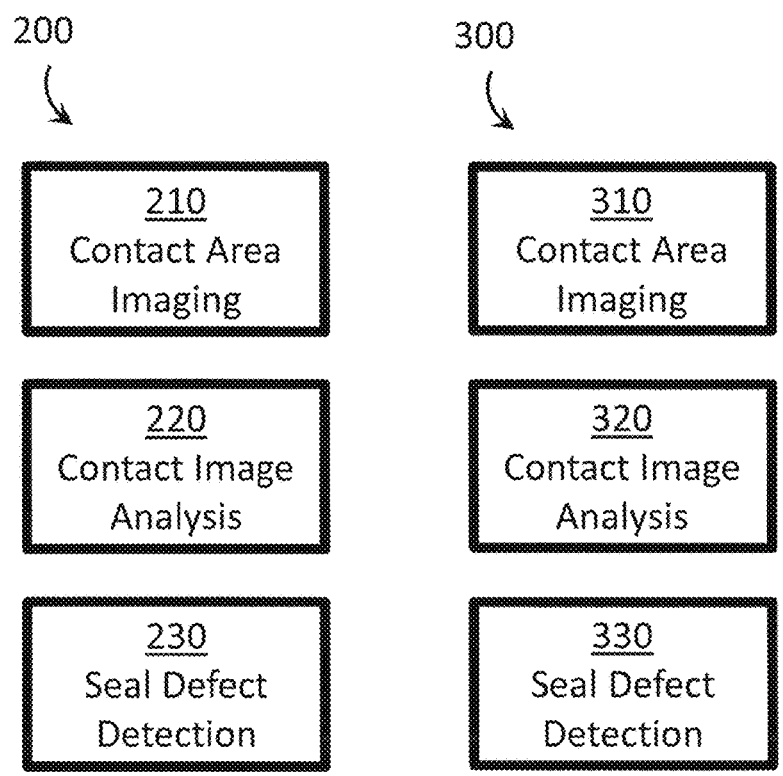

SYSTEMS AND METHODS FOR DETECTING SYRINGE SEAL DEFECTS

FIELD

The present disclosure relates generally to methods for inspecting syringes, and more specifically, to systems and methods for detecting seal defects in syringes.

BACKGROUND

Syringes used for delivery of medicaments are principally constructed of a barrel and a stopper. The stopper is slidably fitted within the syringe barrel and may have a plunger rod affixed to it for actuation of the syringe and delivery of medicament. The stopper is generally constructed of an elastomer, with silicone oil applied. The silicone oil is applied to reduce sliding friction between the stopper and barrel and to improve the seal between them. The oil, allows for ease of sliding when administering a dose which ensures the full dose can be administered. This is particularly critical in the case of pens and so-called auto injecting syringes. The oil is also critical to prevent jamming of the device which can lead to trauma at the site of injection.

Though silicone oil has traditionally been utilized in syringes, such use can be problematic. In pharmaceutical applications, the use of silicone oil is particularly concerning. For example, the silicone oil may undesirably degrade medicine contained in the syringe and may cause aggregation of certain proteins in the medicines.

One concern for both lubricated and non-lubricated syringes is that of an effective seal between the stopper and the syringe barrel. Lack of an effective seal can lead to reduced shelf life and/or contamination, for example. Accurate methods of determining effective seals either prior to, or following filling of a syringe (a "pre-filled" syringe) remain to be realized.

SUMMARY

Various aspects of the instant disclosure relate to inspection systems and methods for detecting seal defects in syringes, and in particular detecting seal defects in non-lubricated syringes.

Some embodiments relate to a method of inspecting a dry, non-lubricated syringe. The method includes optically imaging a contact area between a stopper positioned in a syringe barrel of a dry, non-lubricated syringe to form a contact image. The contact image includes a seal line correlating to the engagement between a seal area of the stopper and the inner diameter of the syringe barrel. The method also includes analyzing the contact image for discontinuities in seal line and determining if the syringe exceeds a defect criteria based upon the discontinuities.

Some embodiments relate to a method of inspecting a wet, non-lubricated syringe. The method includes optically imaging a contact area between a stopper positioned in a syringe barrel of a wet, non-lubricated syringe to form a contact image. The contact image includes a seal line correlating to a seal area of the stopper and an indicating line correlating to an indicating area of the stopper. The method also includes analyzing the indicating line of the contact image to detect contact between the indicating area and the syringe barrel, and determining if the syringe exceeds a defect criteria based upon the detected contact between the indicating area and the syringe barrel.

Some embodiments relate to a method of inspecting a dry, non-lubricated syringe. The syringe includes a barrel having an inner diameter and an outer diameter with a stopper inserted therein, the stopper having a seal area. The method also includes optically imaging a contact area between the stopper and the inner diameter of the barrel to form a contact image, the contact image including a line correlating to contact between the seal area and the inner diameter of the barrel and visually inspecting the contact image. The syringe is considered defective if the line is discontinuous.

Some embodiments relate to a method of inspecting a non-lubricated syringe. The syringe includes a barrel having an inner diameter and an outer diameter with a stopper inserted therein. The stopper has a seal area and an indicating area adjacent to the seal area. The method also includes optically imaging a contact area between the stopper and the inner diameter of the barrel to form a contact image. The contact image includes a line having a width correlating to contact between the seal area and the inner diameter of the barrel. The method also includes visually inspecting the contact image, wherein the syringe is defective if a color of the line and indicating area are substantially the same.

Some embodiments relate to a method of inspecting a wet, non-lubricated syringe. The syringe includes a barrel having an inner diameter and an outer diameter, with a stopper inserted therein, the stopper having a first seal area, a second seal area, and an indicating area therebetween. The method also includes optically imaging a contact area between the stopper and the inner diameter of the barrel to form a contact image. The contact image includes a first line correlating to contact between the first seal area and the inner diameter of the barrel and a second line correlating to contact between the second seal area and the inner diameter of the barrel. The space between the first line and the second line correlates to the indicating area. The method also includes visually inspecting the contact image, where the syringe is defective if color in the indicating area extends between the first and second lines.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 6 is a schematic representation of a method, of inspecting a dry (unfilled), non-lubricated syringe such as that of FIG. 1, according to some embodiments;

FIG. 7 is a schematic representation of a method of inspecting a wet (filled), non-lubricated syringe such as that of FIG. 1, according to some embodiments;

DETAILED DESCRIPTION

Figure 1:
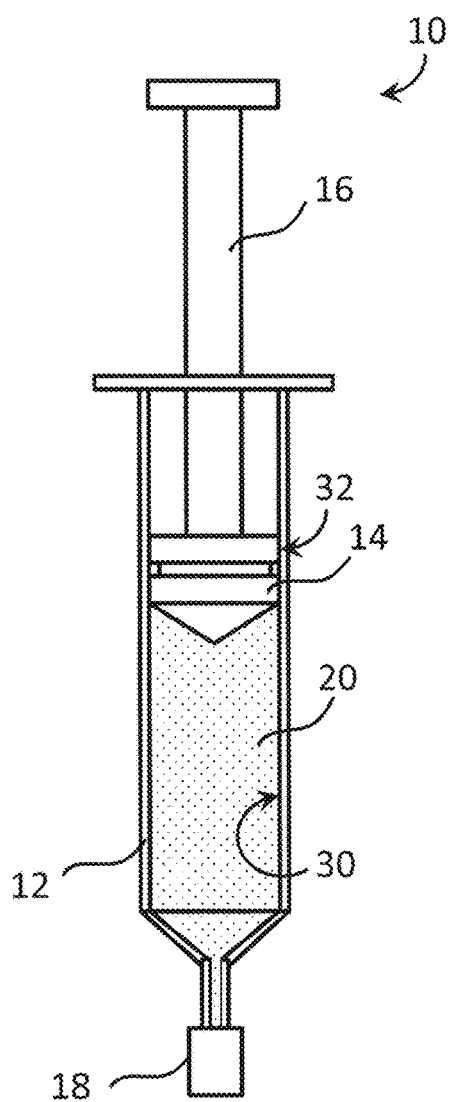
FIG. 1 is a schematic view of a syringe according to some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. It is to be appreciated that the terms "stopper" and "syringe stopper" may be used interchangeably herein.

FIG. 1 is a schematic view of an exemplary syringe 10. As shown, the syringe 10 includes a syringe barrel 12, a stopper 14 that forms a complementary fit with the syringe barrel 12, a plunger rod 16, a tip cap or needle shield 18, and, in the case of a pre-filled embodiment, a liquid 20, such as a medicament, for dispensing from the syringe 10. Although the syringe 10 is shown as a "wet" system (i.e., a fluid is contained in the syringe barrel 12 for dispensing), various embodiments will be described in association with "dry" systems (i.e., one in which a fluid has not yet been introduced, into the syringe barrel 12 for dispensing).

As shown, the syringe barrel 12 and the stopper 14 are first and second complementary syringe components that are slidably engaged with one another, the stopper 14 is intended to form a slidable seal within the syringe barrel 12. Although the syringe barrel 12 and the stopper 14 are slidably engaged in a linear relationship, it should be understood that other sliding relationships (e.g., rotational sliding between a valve body and a valve plug) are considered to be within the scope of the invention.

The syringe barrel 12 defines a bore or inner surface 30, also described as a sliding surface. In some embodiments, the syringe barrel 12 includes a substantially rigid or hard material, such as a glass material (e.g., borosilicate glass), a ceramic material, one or more polymeric materials (e.g., polypropylene, polyethylene, and copolymers thereof), a metallic material, or a plastic material (e.g., cyclic olefin polymers (COC) and cyclic olefin copolymers (COP), and combinations thereof. Although any of a variety of glass compositions are contemplated, borosilicate glass has been shown to been effective material in association with friction-reduction methods according to some embodiments. As, understood with reference to the associated inspection systems and methods subsequently described, the syringe barrel 12 is generally formed of an optically transmissive material, at least in the area in which the stopper 14 and barrel 12 are in contact, or engaged, with one another.

As indicated in FIG. 1, the stopper 14 defines an outer surface 32 for slidably engaging the inner surface 30 of the syringe barrel 12. In some embodiments, the stopper 14 includes a softer material than the syringe barrel 12. For example, the stopper 14 may be constructed with one or more barrier films applied to an elastomeric core, where the barrier film(s) define the outer surface 32 of the stopper 14. The elastomeric core can be formed of a variety of elastomeric materials, such as, but not limited to, rubbers constructed from butyl, bromobutyl, chlorobutyl, silicone, nitrile, styrene butadiene, polychloroprene, ethylene propylene diene, fluoroelastomers, thermoplastic elastomers (TPE), thermoplastic vulcanizates (TPV), silicon, and materials sold under the trade name VITON® and combinations and blends thereof. Exemplary elastomeric materials include, but are not limited to, butyl rubber, bromobutyl rubber, chlorobutyl rubber, silicone, nitrile, styrene butadiene, polychloroprene, ethylene propylene diene, fluoroelastomers and combinations thereof.

Non-limiting examples of suitable barrier films include fluoropolymer films and densified expanded fluoropolymer films, such as, but not limited to, polytetrafluoroethylene (PTFE) and densified expanded polytetrafluoroethylene (ePTFE) films, fluorinated ethylene propylene (FEP), polyethylene, polypropylene, polyvinylidene fluoride, polyvinylfluoride, perfluoropropylevinylether, perfluoroalkoxy polymers, tetrafluoroethylene hexafluoropropylene vinylidene fluoride terpolymer (THV) and copolymers and combinations thereof.

Barrier films based on ePTFE provide for thin and strong barrier layers to leachables and extractables. Expanded polytetrafluoroethylene (ePTFE) films prepared in accordance with the methods described in U.S. Pat. No. 7,521,010 to Kennedy et al., U.S. Pat. No. 6,030,694 to Dolan et al., U.S. Pat. No. 5,792,525 to Fuhr et al., or U.S. Pat. No. 5,374,473 to Knox et al., may be used herein. In addition, expanded copolymers of PTFE, such as are described in U.S. Pat. No. 5,708,044 to Branca, U.S. Pat. No. 6,541,589 to Baillie, U.S. Pat. No. 7,531,611 to Sabot et al., U.S. Pat. No. 8,637,144 to Ford, and U.S. Pat. No. 9,139,669 to Xu, et al. may be utilized if they are densified.

The barrier film may also include an expanded polymeric material including a functional tetrafluoroethylene (TFE) copolymer material having a microstructure characterized by nodes interconnected by fibrils, where the functional TFE copolymer material includes a functional copolymer of TFE and PSVE (perfluorosulfonyl vinyl ether), or TFE with another suitable functional monomer, such as, but not limited to, vinylidene fluoride (VDF), vinyl acetate, or vinyl alcohol. The functional TFE copolymer material may be prepared, for example, according to the methods described in U.S. Pat. No. 9,139,669 to Xu et al, or U.S. Pat. No. 8,658,707 to Xu et al.

The barrier film may also include a composite fluoropolymer film having a barrier layer and a porous layer. The porous layer, for example, maybe formed of ePTFE or other porous expanded and fibrilizing fluoropolymers (for example, ePTFE as taught in U.S. Pat. No. 6,541,589 to Baille). The ePTFE layers may be filled with an organic or inorganic material to provide color, lubricity, or other function.

Figures 2, 3:
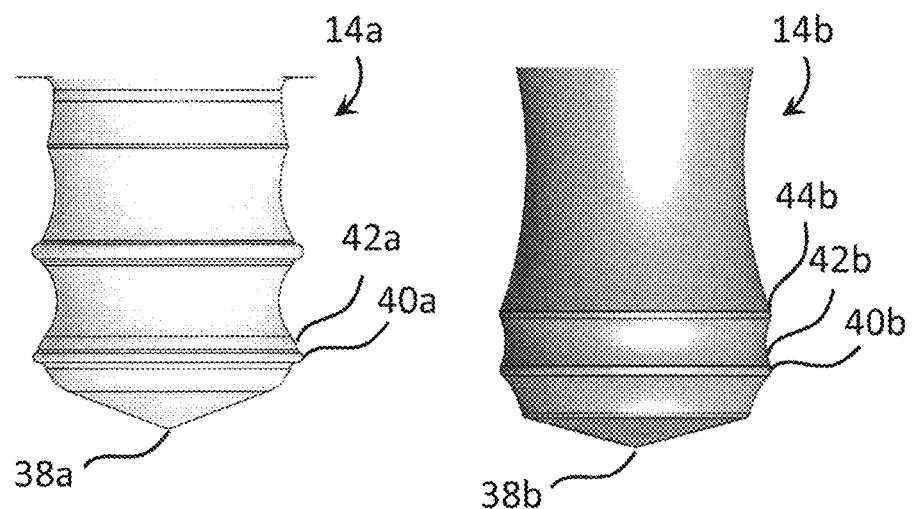
FIG. 2 shows a portion of a stopper of the syringe of FIG. 1, according to some embodiments.
FIG. 3 shows a portion of another stopper of the syringe of FIG. 1, according to some embodiments.

The stopper 14 can have a variety of configurations. FIG. 2 shows a portion of a stopper 14a for use as the stopper 14 in the syringe 10. As shown, the stopper 14a has a distal end 38a that is intended to be oriented toward the tip of the syringe barrel 12 and in a direction of the fluid that is, or will be contained in the syringe barrel 12. The stopper 14a includes a sealing area 40a corresponding to a raised sealing rib defining a slightly increased diameter of the stopper 14a, Although a single sealing area is called out, it should be understood that any number of sealing ribs can be employed as desired (in fact, FIG. 2 shows another sealing rib proximal to the sealing rib corresponding to sealing area 40a). The stopper 14a also includes an indicating area 42a that is immediately adjacent to the sealing area 40a, As shown, the indicating area 42a has a slightly smaller diameter than the sealing area 40a, Again, although a single indicating area is called out in association with the distal most sealing area 40a, it should be understood that any number of indicating areas, at any longitudinal position and in association with any sealing area, can be employed as desired, and that such embodiments are considered to be within the purview of the invention.

The indicating area 42a is generally an area adjacent to the foremost, or most distal, sealing area (sealing area 40a in FIG. 2). As shown, the indicating area 42a is configured to exhibit a contact pressure with the syringe barrel 12 that is lower than the contact pressure between the sealing area 40a and the syringe barrel 12 and is lower than that required to form a liquid tight seal. The indicating area 42a is configured, in the presence of liquid such as would occur when the foremost seal is breached, to wick the liquid and create a noticeable change in the appearance of the indicating area 42a when optically imaged. In some embodiments, the indicating area 42a is an area of low pressure contact pressure between the stopper 14a and the syringe barrel 12, such as less than about 1 MPa.

In some embodiments, the indicating area 42a is configured to be spaced from the syringe barrel 12 (i.e., not in direct contact with the syringe barrel 12), but is sufficiently proximate to the syringe barrel 12 such that upon a leak through the sealing area 40a, liquid will enter the indicating area by capillary action. In some embodiments, the space is less than about 0.1 mm, although a variety of spaces, or gap sizes, are contemplated depending on the fluid surface tension and viscosity, for example.

FIG. 3 shows a portion of another stopper 14b for use as the stopper 14 in the syringe 10, according to some embodiments. As shown, the stopper 14b has a distal end 38b that is intended to be oriented toward the tip of the syringe barrel 12 and in a direction of the fluid that is, or will be contained in the syringe barrel 12. The stopper 14b includes a sealing area 40b corresponding to a raised sealing rib defining a slightly increased diameter of the stopper 14b. Although a single sealing area is called out, it should be understood that any number of sealing ribs can be employed as desired (FIG. 3 shows a second, more proximal sealing rib forming sealing area 44b). The stopper 14b includes an indicating area 42b that is located between two sealing ribs and positioned proximal and adjacent to the sealing area 40b. As shown, the indicating area 42b has a slightly smaller diameter than the sealing area 40b. Again, although a single indicating area is called out, it should be understood that any number of indicating areas, at any longitudinal position, can be employed as desired and such embodiments are considered to be within the purview of the invention.

As shown in FIG. 3, the indicating area 42b is located between two sealing areas, 40b, 44b and is configured to exhibit a contact pressure with the syringe barrel 12 that is lower than the contact pressure between the sealing area 40b and the syringe barrel 12 and is also lower than that required to form a liquid tight seal (e.g., less than about 1 MPa). The indicating area 42b is configured to wick liquid when the seal of the sealing area is defective to create a noticeable change in the appearance of the indicating area 42b when optically imaged.

Rather than low contact pressure, all or a portion of the indicating area 42b may be configured to be spaced from the syringe barrel 12 (e.g., greater than zero but less than about 0.1 mm). In such instances, the indicating area or portions thereof encourage fluid to enter the indicating area by capillary action to provide a visible indication of a leak.

Figure 4:
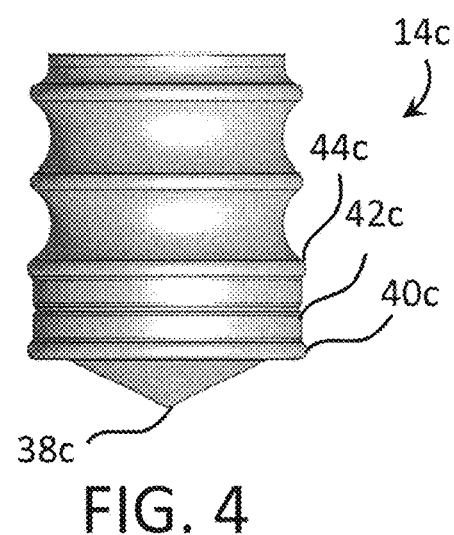
FIG. 4 shows a portion of another stopper of the syringe of FIG. 1, according to some embodiments.

FIG. 4 shows a portion of another stopper 14c for use as the stopper 14 in the syringe 10. As shown, the stopper 14c has a distal end 38c intended to be oriented toward the tip of the syringe barrel 12 and in a direction of the fluid that is, or will be contained in the syringe barrel 12. The stopper 14c includes a distal most sealing area 40c and another sealing area 44c, each of the sealing areas 40c, 44c corresponding to a raised sealing rib defining a slightly increased diameter of the stopper 14c. It should be understood that any number of sealing areas are employed as desired, and that such embodiments are considered to be within the scope of the invention. The stopper 14c also includes an indicating area 42c located between the two sealing ribs and positioned proximal to and adjacent the sealing area 40c. As shown, the indicating area 42c has a slightly smaller diameter than the sealing area 40c, Additionally, as depicted, the indicating area 42c includes a relatively flat, or non-tapered configuration in comparison to sealing areas 40c, 44c. Again, although a single indicating area is called out, it should be understood that any number of indicating areas, at any longitudinal position can be employed as desired and that such embodiments are considered to be within the purview of the invention.

As, shown in FIG. 4, the indicating area 42c is configured to be spaced from the syringe barrel 12 (i.e., not in direct contact with the syringe barrel 12), but is sufficiently proximate to the syringe barrel 12 such that upon a leak through the sealing area 40c liquid will enter the indicating area by capillary action. In some embodiments, the space is less than about 0.1 mm, although a variety of spaces, or gap sizes, are contemplated, depending on the fluid surface tension and viscosity, for example. Additionally, or as an alternative, the indicating area 42c or a portion thereof can be configured to exhibit a reduced contact pressure (e.g., less than about 1 MPa) to wick liquid when the seal of the sealing area is defective to create a noticeable change in the appearance of the indicating area 42b when optically imaged.

Figure 5:
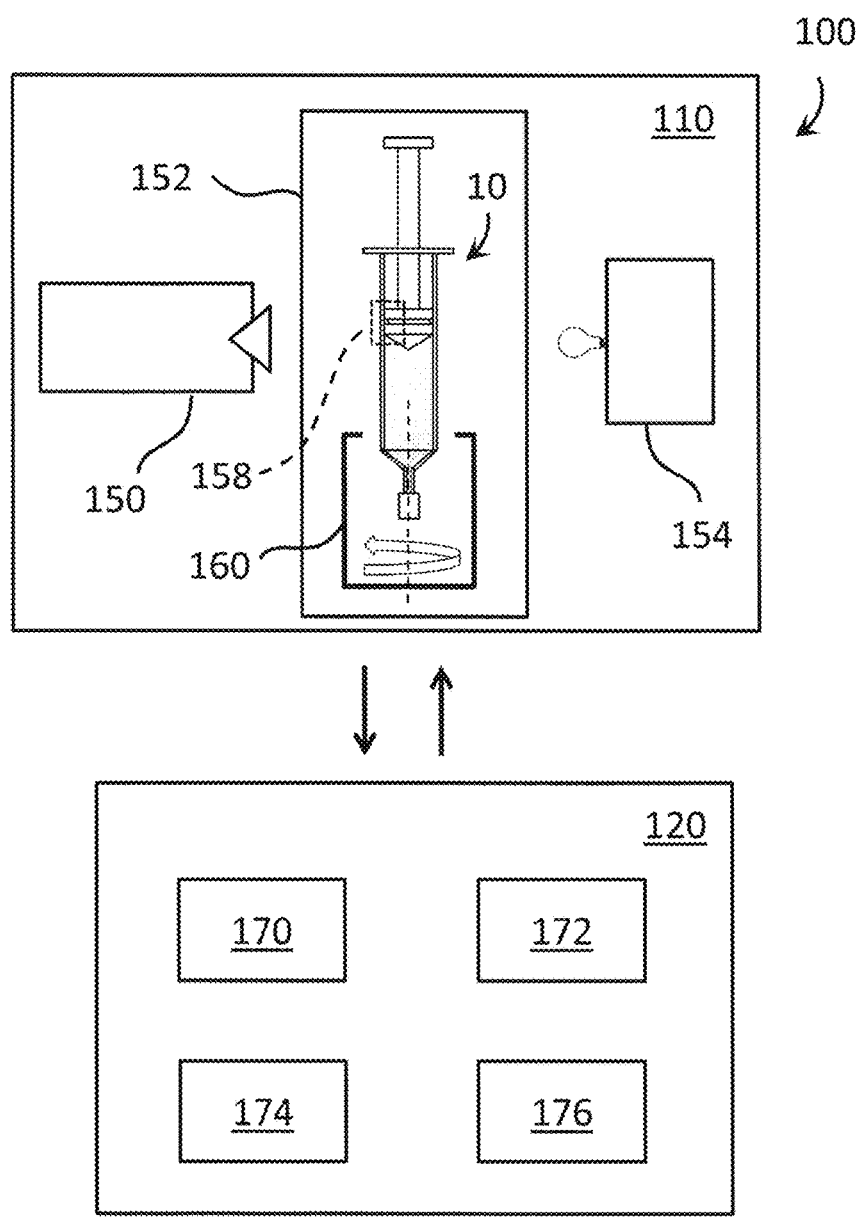
FIG. 5 is a schematic representation of a system for optically imaging the syringe of FIG. 1, according to some embodiments.

FIG. 5 is a schematic representation of a system 100 for optically imaging the syringe 10 in either a wet (filled) or dry (unfilled) state as desired. The system 100 includes an imaging module 110 for imaging the seal and/or indicating areas of the syringe 10 and a control module 120 for controlling image data acquisition by the imaging module 110 and processing the image data. The imaging module 110 includes an imaging apparatus 150, a stage apparatus 152, and a lighting apparatus 154.

The imaging apparatus 150 is optionally a line scan camera, such as a KEYENCE model XG-HL04M line scan camera or a TDI line scan camera, for continuous imaging, including acquisition of grayscale and/or color image data as desired. The imaging apparatus 150 may also be a digital microscope, such as a model VHX-100E sold under the trade name "KEYENCE". In still other embodiments, the imaging apparatus 150 is a digital camera such as KEYENCE XG-200M. The imaging apparatus 150 is configured to acquire image pixel data in a contact area 158 at the syringe 10 where the stopper 14 contacts the inner diameter of the syringe barrel 12. In some embodiments, the imaging apparatus 150 is configured to acquire image data along, a line that is substantially tangential to a line of contact between the stopper 14 and the syringe barrel 12.

The stage apparatus 152 includes a rotation fixture 160 for maintaining the syringe 10 during imaging and for rotating the syringe 10 about a central longitudinal axis of the syringe during imaging. In other embodiments, the stage apparatus 152 is configured to rotate the imaging apparatus 150 about the syringe 10. For example, the stage apparatus optionally includes a rotation fixture 160 such as that sold under the tradename "ORIENTAL MOTOR" model DG60-ARAKD-3.

The lighting apparatus 154 may be configured for brightfield illumination, darkfield illumination, strobed illumination, continuous illumination and combinations thereof. Any such embodiments are within the scope of the invention.

In some embodiments, the control module 120 includes hardware and software for acquiring and processing image data from the imaging module. In some embodiments, the control module 120 includes a camera controller 170 for sending and receiving camera control signals, a lighting controller 172 for sending and receiving lighting control signals, a stage controller 174 for sending and receiving stage control signals, and an image processor 176 for receiving and processing acquired image data. The control module 120 optionally includes one or more user interfaces (e.g., a keyboard, mouse, or touchscreen), one or more user displays (e.g., a monitor), and other hardware and software as desired.

FIG. 6 is a schematic representation of a method 200 of inspecting a dry, non-lubricated syringe 10. In a "wet" system (i.e., one in which a liquid is present in the barrel 12), a "non-lubricated" system 10 does not include a fluid for lubrication (e.g., silicone oil) between the stopper 14 and the barrel 12 in addition to the fluid contained by the barrel 12 of the system 10 (e.g., a medicament). In a "dry" system, (i.e., one in which a liquid is not present in the barrel 12), a "non-lubricated" system does not include a fluid for lubrication (e.g., silicone oil) between the stopper 14 and the barrel 12. The method includes contact area imaging 210, contact image analysis 220, and seal defect detection 230. The method may be performed using the inspection system 100.

Contact area imaging 210 includes optically imaging the contact area 158 to produce a contact image (i.e., contact image data) including an optically detectable seal line correlating to the engagement between, a seal area (e.g., seal areas 40a, 40b, or 40c) of the stopper 14 and the inner diameter of the syringe barrel 12. In some embodiments, the contact area 158 is imaged with a line scan camera. The contact area is optionally imaged by taking a plurality of images, or scans, of the contact area about the entire circumference of the syringe 10 (e.g., through at least one complete revolution of the syringe 10). If desired, the contact, area can be continuously scanned as the syringe 10 is rotated. The image data is optionally greyscale image data or color image data as desired.

Contact image analysis 220 includes analyzing the contact image for discontinuities in the seal line. In some embodiments, discontinuities in the seal line appear as differences in contrast and/or color between a "good" seal, or a desired degree of sealing contact, and a discontinuity, or undesirable amount of sealing contact between the stopper 14 and barrel 12. As shown in the examples that follow, the seal line generally corresponds to a darker line or a line of a first color and discontinuities show up as lighter, areas, or areas of a different color. Manual, visual inspection and/or data processing techniques may be used as desired to locate, quantify, and/or enhance the seal line and seal line discontinuities in the contact image data, including applying image filters, edge detectors, and other data imaging techniques.

Seal defect detection 230 includes determining if the syringe 10 exceeds a defect criteria based upon the discontinuities. In some embodiments, the defect criteria include one or more discontinuities extending across the width of the entire seal line (indicating a path for fluid to travel from one side of the seal line to the other side of the seal line). The defect criteria can also include additional defect parameters, such as total defect area, total number of discrete defects detected across the seal line, or others.

FIG. 7 is a schematic representation of a method 300 of inspecting a wet, non-lubricated syringe 10. The method includes contact area imaging 310, contact image analysis 320, and seal defect detection 330. As with method 200, method 300 may be performed using the inspection system 100.

In some embodiments, contact area imaging 310 includes optically imaging the contact area 158 between stopper 14 and syringe barrel 12 with a liquid (e.g., medicament) present in the system 10. The contact area is imaged to produce a contact image (i.e., contact image data) that includes a seal line correlating to the engagement between a seal area (e.g., seal areas 40a, 40b, or 40c) of the stopper 14 and the inner diameter of the syringe barrel 12. In some embodiments, the contact image includes an indicating line correlating to an indicating area (e.g., indicating areas 42a, 42b, 42c) of the syringe 10. The indicating line image data may be compared to the seal line data. If the seal line includes one or more areas that are the same color or contrast as the indicating line, those areas can be identified as defect areas. In this manner, the indicating area is optionally used as a calibration for reduced or no contact between the stopper 12 and barrel 14. For reference, the indicating line or portions thereof may only be present in the event of an actual defect in the seal.

In some embodiments, the contact area 158 is imaged with a line scan camera. The contact area is optionally imaged by taking a plurality of images, or scans, of the contact area about the entire circumference of the syringe 10 (e.g., through at least one complete revolution of the syringe 10). If desired, the contact area can be continuously scanned as the syringe 10 is rotated. The image data is optionally greyscale image data or color image data as desired.

In some embodiments, contact image analysis 320 includes analyzing the indicating line of the contact image to detect contact between the indicating area, and the syringe barrel. As previously described, in the presence of a seal defect in a wet system, the indicating area will show greater contact in that fluid will wick or otherwise move into the indicating area between the syringe barrel 12 and the stopper 14. As shown in the examples that follow, in the event of a good, or non-defective seal, the seal line generally corresponds to a darker line or a line of a first color and the indicating line shows as lighter areas or areas of a different color.

In some embodiments, the indicating line includes at least one of color and intensity data, and analyzing the indicating line of the contact image to detect contact between the indicating area and the syringe barrel includes determining whether at least one of the color and intensity data exceeds a threshold value. In the event of a leak, the indicating line shows darker than normal, or is similar in darkness or color to the seal line. In the instance of color image data, some methods include comparing a color of the indicating line to a color of the seal line. Manual, visual inspection and/or data processing techniques may be used as desired to locate, quantify, and/or enhance the seal line and indicating line in the contact image data, including applying image filters, edge detectors, and other data imaging, techniques.

Seal defect detection 330 includes determining if the syringe 10 exceeds a defect criteria based upon the detected contact between the indicating area (e.g., indicating areas 42a, 42b, 42c) and the syringe barrel 12. In some embodiments, the defect criteria include the width of the detected indicating line exceeding a predetermined threshold (e.g., an expected indicating line width). In some embodiments, the defect criteria include detecting the presence or absence of an indicating line (e.g., where the indicating area does not contact the syringe barrel in the absence of fluid presence), the color, intensity or contrast between the indicating line and the seal line being within a selected threshold limit, or the color intensity or contrast, for example, of the indicating line being above a selected threshold limit.

Figure 8:
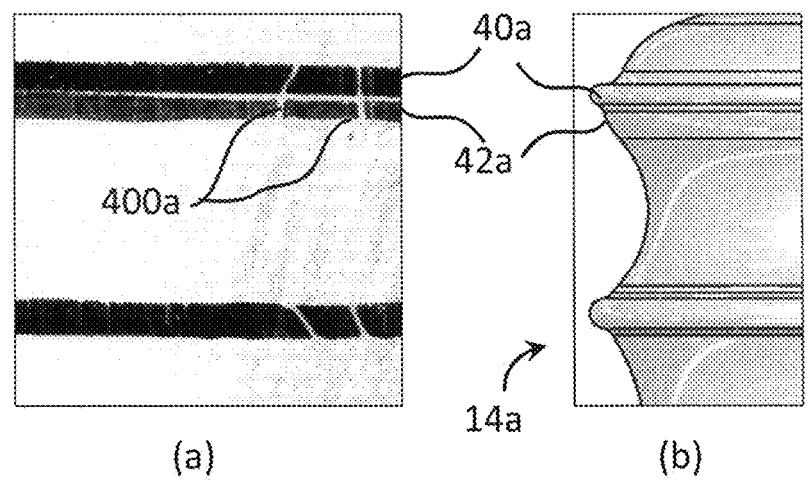
FIG. 8 shows a portion of a contact image and contact area of the stopper of FIG. 2 of the syringe system in a dry state, according to some embodiments.

FIG. 8 shows a portion of a contact image (FIG. 8(a)) of the contact area corresponding to, stopper 14a in a dry, non-lubricated syringe system 10. As shown, the contact image of the contact area 158 (FIG. 5) includes a seal line correlating to seal area 40a and an indicating line correlating to indicating area 42a. In the contact image of FIG. 8(a), several defects in the form of discontinuities 400a extending across both the seal line, and the indicating line are shown. The contact image was taken using continuous imaging with a line scan camera of the contact area as the syringe 10 was rotated to image the contact area about the entire circumference of the syringe 10.

Figure 9:
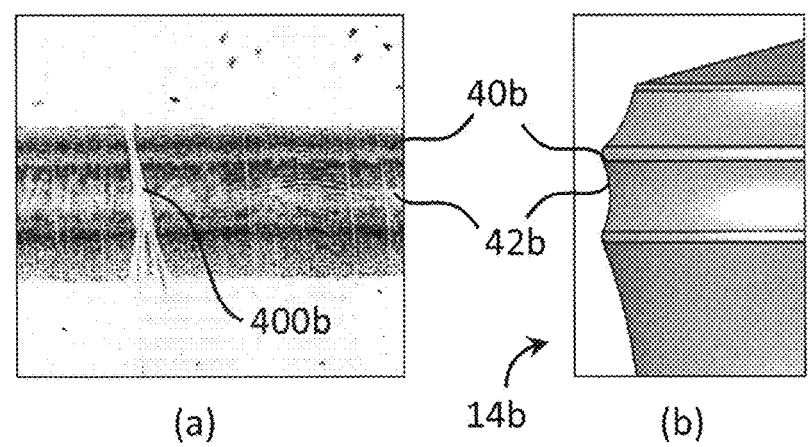
FIG. 9 shows a portion of a contact image and contact area of the stopper of FIG. 3 in the syringe system in a dry state, according to some embodiments.

FIG. 9 shows a portion of a contact image (FIG. 9(a)) of the contact area corresponding to stopper 14b in a dry, non-lubricated syringe system. As shown, the contact image of the contact area includes a seal line correlating to seal area 40b and an indicating line correlating to indicating area 42b. In the contact image of FIG. 9(a), several defects in the form of discontinuities 400b are shown extending across both the seal line and the indicating line. The contact image was taken using continuous imaging with a line scan camera of the contact area as the syringe was rotated to image the contact area about the entire circumference of the syringe 10. In some embodiments, the system 100 (FIG. 5) is configured to acquire such contact image data.

Figure 10:
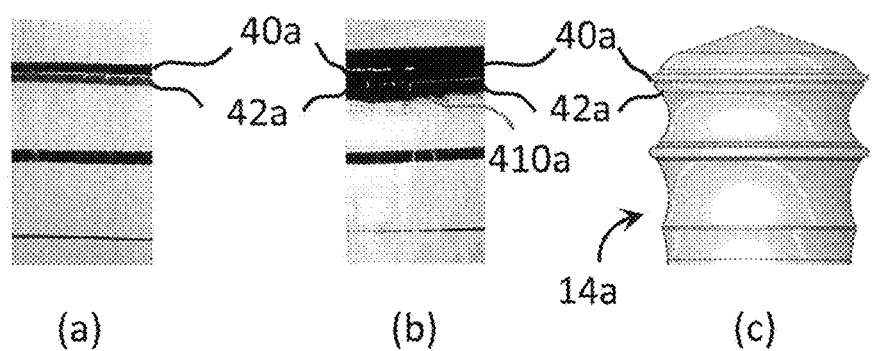
FIG. 10 includes various representations of a syringe including the stopper of FIG. 2, according to some embodiments.

FIG. 10 includes contact images of a syringe 10 including the stopper 14a as well as an image of the stopper 14a for reference purposes. FIG. 10(a) is a contact image of the stopper 14a without fluid present (dry). The dry image of FIG. 10(a) illustrates the indicating line in a non-defective system (i.e., where there is a "good" seal). FIG. 10(b) is a contact image with fluid present (wet). FIG. 10(c) shows the contact area of the stopper 14a for reference purposes. As identified by reference 410a in FIG. 10(b), the indicating line is considerably wider and darker in the presence of a defect (not shown) in the seal, area 40a. The darker, wider indicating line at the indicating area 42a is a result of fluid passing the seal area 40a. The seal line also appears somewhat darker and wider due to the presence of fluid distal to, or in front of, the seal area in comparison to the dry image of FIG. 10(a). Thus, detection of a defect according to some, embodiments includes analyzing one or more of the darkness and width of the indicating line. The contact images of FIGS. 10(a) and 10(b) were obtained using continuous imaging with a line scan camera of the contact area as the syringe 10 was rotated to image the contact area about the entire circumference of the syringe 10. In some embodiments, the system 100 (FIG. 5) is configured to acquire such contact image data.

Figure 11:
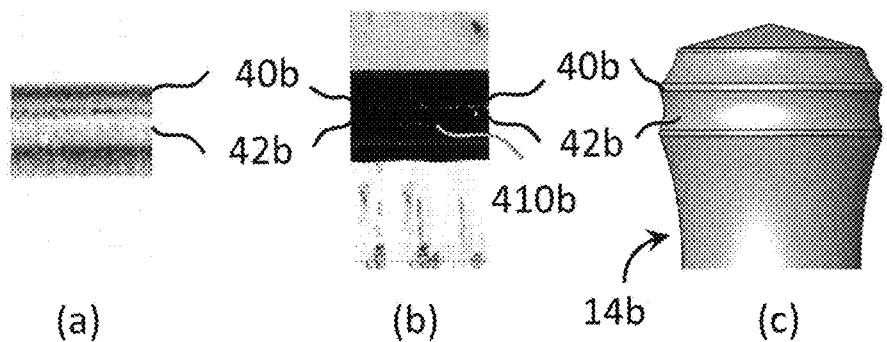
FIG. 11 includes various representations of a syringe including the stopper of FIG. 3, according to some embodiments.

FIG. 11 includes various representations of a syringe 10 including the stopper 14b. FIG. 11(a) is a contact image of the stopper 14b without fluid present (dry). For reference purposes, the dry image of FIG. 11(a) illustrates how the indicating line should generally appear in a non-defective system where there is a "good" seal). FIG. 11(b) is a contact image with fluid present (wet). FIG. 11(c) shows the contact area of the stopper 14b for reference purposes. As identified by reference 410b in FIG. 11(b), the indicating line is considerably darker in the presence of a defect (not shown) in the seal area 40b. The darker, wider indicating line at the indicating area 42b is a result of fluid passing the seal area 40b. The seal line also appears somewhat darker and wider due to the presence of fluid distal to, or in front of, the seal area in comparison to the dry image of FIG. 11(a). Thus, detection of a defect according to some embodiments includes analyzing the darkness of the indicating line (e.g., in comparison to a dry image or in comparison to the seal line). The contact images of FIGS. 11(a) and 11(b) were obtained using continuous imaging with a line scan camera of the contact area as the syringe 10 was rotated to image the contact area about the entire circumference of the syringe 10. In some embodiments, the system 100 (FIG. 5) is configured to acquire such contact image data.

Figure 12:
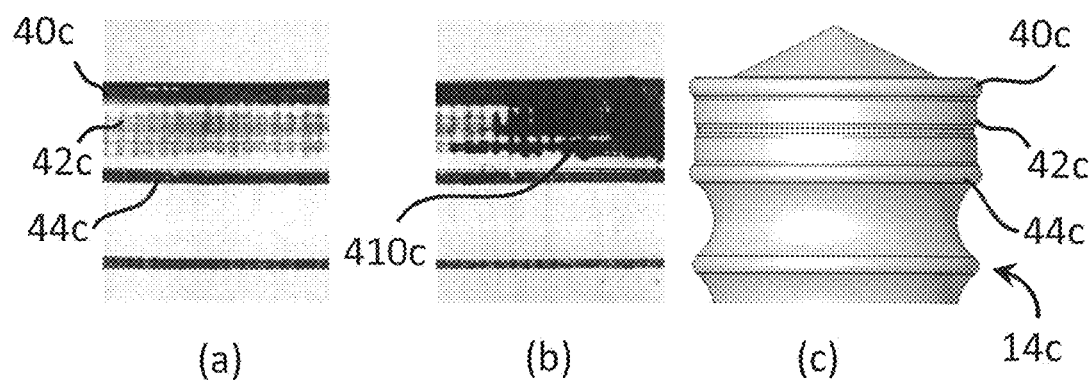
FIG. 12 includes various representations of a syringe including the stopper of FIG. 4, according to some embodiments.

FIG. 12 includes various representations of a syringe 10 including the stopper 14c. FIG. 12(a) is a contact image of the stopper 14b without fluid present (dry). For reference purposes, the dry image of FIG. 12(a) illustrates how the indicating line should generally appear in a non-defective system (i.e., where there is a "good" seal). FIG. 12(b) is a contact image with fluid present (wet). As identified by reference 410c in FIG. 12(b) the indicating line includes regions that are considerably darker in the presence of a defect (not shown) in the seal area 40b, FIG. 12(c) shows the contact area of the stopper 14b for reference purposes.

As shown in FIG. 12(b), the darker indicating line at the indicating area 42c is a result of fluid passing the seal area 40c. The seal line also appears somewhat darker and wider due to the presence of fluid distal to, or in front of, the seal area in comparison to the dry image of FIG. 12(a). Thus, detection of a defect according to some embodiments includes analyzing the darkness of the indicating line (e.g., in comparison to a dry image or in comparison to the seal line). For reference, the term "line" as used in association with the various contact images is meant to correspond to the indicating area, or region of the contact image where the indicating are is expected based upon stopper design. For example, in FIGS. 12(a) and 12(b) the indicating "line" corresponds to the area between the first seal area 40c and the second seal area 44c. The contact images of FIGS. 12(a) and 12(b) were obtained using continuous imaging with a line scan camera of the contact area as the syringe 10 was rotated to image the contact area about the entire circumference of the syringe 10. In some embodiments, the system 100 (FIG. 5) is configured to acquire such contact image data.

Figure 13:
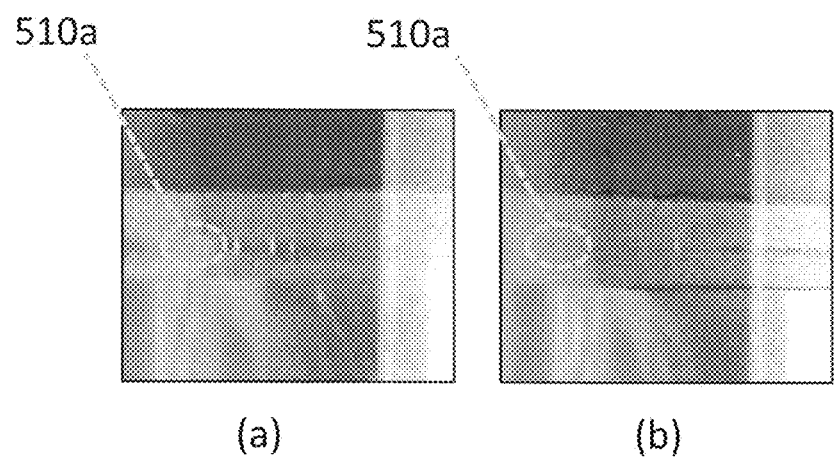
FIG. 13 includes color images of a syringe including the stopper of FIG. 2, according to some embodiments.

FIG. 13 includes color images of a non-defective and defective syringe including the stopper 14a, according to some embodiments. FIG. 13(a) is a wet image of a non-lubricated syringe including the stopper 14a. For reference purposes, the wet image of FIG. 13(a) illustrates how the indicating line (circled with a broken line and indicated by reference 510a) should generally appear in a non-defective system (i.e., where there is a "good" seal). FIG. 13(b) illustrates how the indicating line (circled with a broken line and indicated by reference 510b) could appear in a defective system (i.e., where there is a "bad" seal). As shown, the color of the indicating line differs from that of the seal line above it when the system is non-defective, or does not have a leak. In contrast, the indicating line in FIG. 13(b) is substantially similar to that of the seal line when a defect is present and fluid has passed the seal area 42a of the stopper 14a. The contact images of FIGS. 13(a) and 13(b) were obtained by imaging the contact area, of the syringe using a digital microscope, although it is contemplated and within the scope of the invention that the system 100 may be configured to acquire such color image data about the entire circumference of the syringe.

In another aspect, syringe described herein may be used in combination different therapeutic compounds such as, for example, drugs and biologics, including but not limited to, antibodies, antisense, RNA interference, gene therapy, primary and embryonic stem cells, vaccines, and combinations thereof. For instance, the embodiments described herein may be utilized in combination with any or all of the following:

Cell therapy using cells that are derived primarily from endoderm such as Exocrine secretory epithelial cells and Hormone-secreting cells; ectoderm such as Keratinizing epithelial cells, Wet stratified barrier epithelial cells, Sensory transducer cells, Autonomic neuron cells, Sense organ and peripheral neuron supporting cells, Central nervous system neurons and glial cells, Lens cells; mesoderm such as Metabolism and storage cells, Barrier function cells (lung, gut, exocrine glands, and urogenital tract), Extracellular matrix cells, Contractile cells, Blood and immune system cells, Germ cells, Nurse cell, Interstitial cells or a combination thereof. Additionally cells that are genetically, chemically or physically altered or modified are considered to be in the scope of the invention.

Examples of Exocrine secretory epithelial cells include, but are not, limited to, Salivary gland mucous cell, Salivary gland number 1, Von Ebner's gland cell in tongue, Mammary gland cell, Lacrimal gland cell, Ceruminous gland cell in ear, Eccrine sweat gland dark cell, Eccrine sweat gland clear cell, Apocrine sweat gland cell, Gland of Moll cell in eyelid, Sebaceous gland cell, Bowman's gland cell in nose, Brunner's gland cell in duodenum, Seminal vesicle cell, Prostate gland cell, Bulbourethral gland cell, Bartholin's gland cell, Gland of Littre cell, Uterus endometrium cell, Isolated goblet cell of respiratory and digestive tracts, Stomach lining mucous cell, Gastric gland zymogenic cell, Gastric gland oxyntic cell, Pancreatic acinar cell, Paneth cell of small intestine, Type II prieumacyte of lung, Clara cell of lung; Hormone-secreting cells including but not limited to: Anterior pituitary cells, Intermediate pituitary cell, Magnocellular neurosecretory cells, Gut and respiratory tract, cells, Thyroid gland cells. Parathyroid gland cells, Adrenal gland cells, Leydig cell of testes secreting testosterone, Theca interns cell of ovarian follicle secreting estrogen, Corpus luteum cell of ruptured ovarian follicle secreting progesterone, Juxtaglomerular cell, Macula dense cell of kidney, Peripolar cell of kidney, Mesangial cell of kidney, Pancreatic islets; Keratinizing epithelial cells including but not limited to: Epidermal keratinocyte, Epidermal basal cell, Keratinocyte of fingernails and toenails, Nail bed basal cell, Medullary hair shaft cell, Cortical hair shaft cell, Cuticular hair shaft cell, Cuticular hair root sheath cell, Hair root sheath cell of Huxley's layer, Hair root sheath cell of Henies layer, External hair root sheath cell, Hair matrix cell; Wet stratified barrier epithelial cells including but not limited to: Surface epithelial cell of stratified squamous epithelium and basal cell of epithelia of cornea, tongue, oral cavity, esophagus, anal canal, distal urethra and vagina, Urinary epithelium cell; Sensory transducer cells including but not limited to: Auditory inner hair cell of organ of Corti, Auditory outer hair cell of organ of Corti, Basal cell of olfactory epithelium, Cold-sensitive primary sensory neurons, Heat-sensitive primary sensory neurons, Merkel cell of epidermis, Olfactory receptor neuron, Pain-sensitive primary sensory neurons, Photoreceptor cells of retina in eye: Proprioceptive primary sensory neurons, Touch-sensitive primary sensory neurons, Type I carotid body cell, Type II carotid body cell, Type I hair cell of vestibular system of ear, Type II hair cell of vestibular system of ear, Type I taste bud cell; Autonomic neuron cells including but not limited to: Cholinergic neural cell, Adrenergic neural cell, Peptidergic neural cell; Sense organ and peripheral neuron supporting cells including but not limited to: Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Taste bud supporting cell, Olfactory epithelium supporting cell, Schwann cell, Satellite glial cell, Enteric glial cell; Central nervous system neurons and glial cells including but not limited to: Astrocyte, Neuron cells, Oligodendrocyte, Spindle neuron; Lens cells including but not limited to: Anterior lens epithelial cell, Crystallin-containing lens fiber cell; Metabolism and storage cells including but not limited to: Adipocytes: Liver lipocyte; Barrier function cells including but not limited to: Kidney parietal cell, Kidney glomerulus podocyte, Kidney proximal tubule brush border cell, Loop of Henle thin segment cell, Kidney distal tubule cell, Kidney collecting duct cell, Principal cells, Intercalated cells, Type I pneumocyte, Pancreatic duct cell, Nonstriated duct cell, Principal cell, Intercalated cell, Duct cell, Intestinal brush border cell, Exocrine gland striated duct cell, Gall bladder epithelial cell, Ductulus efferens nominated cell, Epididymal principal cell, Epididymal basal cell; Extracellular matrix cells including but not, limited to: Ameloblast epithelial cell, Plenum semilunatum epithelial cell of vestibular system of ear, Organ of Corti interdental epithelial cell, Loose connective tissue fibroblasts, Corneal fibroblasts, Tendon fibroblasts, Bone marrow reticular tissue fibroblasts, Other nonepithelial fibroblasts, Pericyte, Nucleus pulposus cell of intervertebral disc, Cementablasticementocyte, Odontoblastiodontocyte, Hyaline cartilage chondrocyte, Fibrocartilage chondrocyte, Elastic cartilage chondrocyte, Osteoblastiosteocyte, Osteoprogenitor cell, Hyalocyte of vitreous body of eye, Stellate cell of perilymphatic space of ear, Hepatic stellate cell, Pancreatic stelle cell; Contractile cells including but not limited to: Skeletal muscle cell, Satellite cell, Heart muscle cells, Smooth muscle cell, Myoepithelial cell of iris, Myoepithelial cell of exocrine glands; Blood and immune system cells including but not limited to: Erythrocyte, Megakaryocyte, Monocyte, Connective tissue macrophage, Epidermal Langerhans cell, Osteoclast, Dendritic cell, Microglial cell, Neutrophil granulocyte, Eosinophil granulocyte, Basophil granulocyte, Hybridoma cell, Mast cell, Helper T cell, Suppressor T cell, Cytotoxic T cell, Natural Killer T cell, B cell, Natural killer cell, Reticulocyte, Stem cells and committed progenitors for the blood and immune system; Germ cells including but not limited to: Oogonium/Oocyte, Spermatid, Spermatocyte, Spermatogonium cell, Spermatozoon; Nurse cell including but not limited to: Ovarian follicle cell, Sertoli cell, Thymus epithelial cell; Interstitial cells including but not limited to: Interstitial kidney cells and a combination thereof.

Examples of antibodies, antisense, RNA interference, or gene therapy made to protein targets or gene(s) of: Ataxia Telangiectasia Mutated, Tumor Protein p53, Checkpoint kinase 2, breast cancer, susceptibility protein, Double-strand break repair protein, DNA repair protein RAD50, Nibrin, p53-binding protein, Mediator of DNA damage checkpoint protein, H2A histone family member X, Microcephalin, C-terminal-binding protein 1, Structural maintenance of chromosomes protein 1A; Esterases; Phosphatases; Examples of Ion channels include but are not limited to: ligand-gated ion channels, voltage-gated ion channels; Examples of growth factors include but are not limited to: nerve growth factor (NGF), vascular endothelial growth factor (VEGF), platelet-derived growth factor (PDGF), C-fos-induced growth factor (FIGF), platelet-activating factor (PAF), transforming growth factor beta (TGF-β), b, one morphogenetic proteins (BMPs), Activin, inhibin, fibroblast growth factors (FGFs), granulocyte-colony stimulating factor (G-CSF), granulocyte-macrophage colony stimulating factor (GM-CSF), glial, cell line-derived neurotrophic factor (GDNF), growth differentiation factor-9 (GDF9), epidermal growth factor (EGF), transforming growth factor-α (TGF-α), growth factor (KGF), migration-stimulating factor (MSF), hepatocyte growth factor-like protein (HGFLP), hepatocyte growth factor (HGF), hepatoma-derived growth factor (HOGF), Insulin-like growth factors; Examples of G ProteinCoupled Receptors (GPCR) include but are not limited to: Adenosine receptor family, Adrenergic receptor family, Angiotensin II receptor, Apelin receptor, Vasopressin receptor family, Brain-specific angiogenesis inhibitor family, Bradykinin receptor family, Bombesin receptor family, Complement component 3a receptor 1, Complement component 5a receptor 1, Calcitonin receptor family, Calcitonin receptor-like family, Calcium-sensing receptor, Cholecystokinin, A receptor (CCK1), Cholecystokinin B receptor (CCK2), Chemokine (C—C motif) receptor family, Sphingosine 1-phosphate receptor family, Succinic receptor, Choiinergic receptor family. Chemokine-like receptor family, Cannabinoid receptor family, Corticotropin releasing hormone receptor family, prostaglandin D2 receptor, Chemokine C—X3-C receptor family, Chemokine (C—X—C motif) receptor family, Burkitt lymphoma receptor, Chemokine (C—X—C motif) receptor family, Cysteinyl leukotriene receptor 2 (CYSLT2), chemokine receptor (FY), Dopamine receptor family, G protein-coupled receptor 183 (GPR183), Lysophosphatidic acid receptor family, Endothelin receptor family, Coagulation factor II (thrombin) receptor family, Free fatty acid receptor family, Formylpeptide receptor family, Follicle stimulating hormone receptor (FSHR), gamma-aminobutyric acid (GABA) B receptor, Galanin receptor family, Glucagon receptor, Growth hormone releasing hormone receptor (GHRH), Ghrelin receptor (ghrelin), Growth hormone secretagogue receptor 1b (GHSR1b), Gastric inhibitory polypeptide receptor (GIP), Glucagon-like peptide receptor family, Gonadotropin-releasing hormone receptor (GnRH), pyroglutamylated RFamide peptide receptor (QRFPR), G protein-coupled bile acid receptor 1 (GPBA), Hydroxycarboxylic acid receptor family, Lysophosphatidic acid receptor 4 (LPA4) Lysophosphatidic acid receptor 5 (GPR92), G protein-coupled receptor 79 pseudogene (GPR79), Hydroxycarboxylic acid receptor 1 (HCA1), G protein coupled receptor (C5L2, FFA4, FFA4, FFA4, GPER, GPR1, GPR101, GPR107, GPR119 GPR12, GRR123, GPR132, GPR135, PR139, GPR141, GPR142, GPR143, GPR146, GPR148, GPR149, GPR15, GPR150, GPR151, GPR152, GPR157, GPR161, GPR162, GPR17, GPR171, GPR173, GPR176, GPR18, GPR182, GPR20, GPR22, GPR25, GPR26, GPR27, GPR3, GPR31, GPR32, GPR35, GPR37L1, GPR39, GPR4, GPR45, GPR50, GPR52, GPR55, GPR6, GPR61, GPR65, GPR75, GPR78, GPR83, GPR84, GPR85, GPR88, GPR97, TM7SF1), Metabotropic glutamate receptor family, Gastrin releasing peptide receptor (BB2), Orexin receptor family, Histamine receptor family, 5-hydroxytryptamine receptor family, KISS1-derived peptide receptor (kisspeptin), Leucine-rich repeat-containing G protein-coupled receptor family, horiogonaclotropin receptor (LH), Leukotriene B4 receptor (BLT1), Adenylate Cyclase Activating Polypeptide 1 Receptor 1 (mPAC1), Motilin receptor, Meianocortin receptor family, Melanin concentrating hormone receptor 1 (MCH1), Neuropeptide Y1 receptor (Y1), Neuropeptide Y2 receptor (NPY2R), Opioid receptor family, Oxytocin recepter (OT), P2Y Purinoceptor 12 (mP2Y12), P2Y Purinoceptor 6 (P2Y6), Pancreatic polypeptide receptor family, Platelet-activating factor receptor family, Prostaglandin E receptor family, Prostanoid IP1 receptor (IP1), MAS-related GPR, member family, Rhodopsin (Rhodopsin), Relaxin family peptide receptor family, Somatostatin receptor family, Tachykinin receptor family, Melatonin receptor family, Urotensin receptor family, Vasoactive intestinal peptide receptor 1 (mVPAC1), Neuromedin B Receptor (BB1), Neuromedin U receptor 1 (NMU1), Neuropeptides B/W receptor family, Neuropeptide FF receptor 1 (NPFF1), neuropeptide S receptor 1 (NPS receptor), Neuropeptide Y receptor family, Neurotensin receptor 1 (NTS1), Opsin 5 (OPN5), Opiold receptor-like receptor (NOP), Oxoeicosanoid (OXE) receptor 1 (OXE), Oxogiutarate (alpha-ketogiutarate) receptor 1 (OXGR1), Purinergic receptor family, Pyrimidinergic receptor family, Prolactin releasing hormone receptor (PRRP), Prokineticin receptor family, Platelet activating receptor (PAF), Prostaglandin F receptor family, Prostaglandin I2 (prostacyclin) receptor family, Parathyroid hormone receptor family, muscarinic 4 (rM4), Prostanoid DP2 receptor (rGPR44), Prokineticin receptor family, Relaxin family peptide receptor family, Secretin receptor (secretin), Smoothened, Frizzled class receptor (Smoothened), trace amine associated receptor family, Tachykinin family, Thromboxane A2 receptor (TP), Thyrotropin-releasing hormone receptor (TRH1), Thyroid Stimulating Hormone Receptor (TSH); Examples of Protein kinases include but are not limited to: AP2 associated kinase, *Homo sapiens* ABL proto-oncogene 1-non-receptor tyrosine-protein kinase family, c-abl oncogene 1 receptor tyrosine kinase family, v-abl Abelson murine leukemia viral oncogene homolog 2, activin A receptor family, chaperone-ABC1 activity of bc1 complex homolog (*S. pombe*) (ADCK3), aarF domain containing kinase 4 (ADCK4), v-akt murine thymoma viral oncogene homolog family, anaplastic lymphoma receptor tyrosine kinase family, protein kinase A family, protein kinase B family, ankyrin repeat and kinase domain containing 1 (ANKK1), NUAK family-SNF1-like kinase, mitogen-activated protein kinase kinase kinase family aurora kinase A (AURKA), aurora kinase B (AURKB), aurora kinase C (AURKC), AXL receptor tyrosine kinase (AXL), BMP2 inducible kinase (BIKE), B lymphoid tyrosine kinase (BLEB), bone morphogenetic protein receptor family, BMX non-receptor tyrosine kinase (BMX), v-raf murine sarcoma viral oncogene homolog B1 (BRAF), protein tyrosine kinase 6 (BRK), BR serineithreonine kinase family, Bruton agammaglobulinemia tyrosine kinase (BTK), calciumicalmodulin-dependent protein kinase family, cyclin-dependent kinase family, cyclin-dependent kinase-like family, CHK1 checkpoint homolog (*S. pombe*) (CHEK1), CHK2 checkpoint homolog (*S. pombe*) (CHEK2), Insulin receptor, isoform A (INSR), Insulin receptor, isoform B (INSR), rho-interacting serine/threonine kinase (CIT), v-kit Hardy- Zuckerman 4 feline sarcoma viral oncogene homolog (KIT), CDC-Like Kinase family—Hepatocyte growth factor receptor (MET), Proto-oncogene tyrosine-protein kinase receptor, colony-stimulating factor family receptor, c-src tyrosine kinase (CSK), casein kinase family, megakaryocyte-associated tyrosine kinase (CTK), death-associated protein kinase family, doublecortin-like kinase family, discoidin domain receptor tyrosine kinase, dystrophia myotonica-protein kinase (DMPK), dual-specificity tyrosine-(Y)-phosphorylation regulated kinase family, epidermal growth factor receptor family, eukaryotic translation initiation factor 2-alpha kinase 1 (EIF2AK1), EPH receptor family, Ephrin type-A receptor family, Ephrin type-B receptor family, v-erb-b2 erythroblastic leukemia viral oncogene homolog family, mitogen-activated protein kinase family, endoplasmic reticulum to nucleus signaling 1 (ERN1), PTK2 protein tyrosine kinase 2 (FAK), fer (fpsifes related) tyrosine kinase (FER). feline sarcoma oncogene (FES), Fibroblast growth factor receptor family, Gardner-Rasheed feline sarcoma viral (v-fgr) oncogene homolog (FGR), fms-related tyrosine kinase family, Fms-related tyrosine kinase family fyn-related kinase (FRK), FYN oncogene related to SRC, cyclin G associated, kinase (GAK), eukaryotic translation initiation factor 2 alpha kinase, Growth hormone receptor. G protein-coupled receptor kinase 1 (GRK1), G protein-coupled receptor kinase family, glycogen, synthase kinase family, germ cell associated 2 (haspin) (HASPIN), Hemopoietic cell kinase (HCK), homeodomain interacting protein kinase family, mitogen-activated protein kinase kinase kinase kinase family, hormonally up-regulated Neu-associated kinase (HUNK), intestinal cell (MAK-like) kinase (ICK), Insulin-like growth factor 1 receptor (1GF1R), conserved helix-loop-helix ubiquitous kinase (IKK-alpha), inhibitor of kappa light polypeptide gene enhancer in B-cells kinase beta family, insulin receptor (INSR), insulin receptor-related receptor (INSRR), interleukin-1 receptor-associated kinase family, IL2-inducible T-cell kinase (ITK), Janus kinase family, Kinase Insert Domain Receptor, v-kit Hardy-Zuckerman 4 feline sarcoma viral oncogene homolog, lymphocyte-specific protein tyrosine kinase (LCK), LIM domain kinase family, serineithreonine kinase family leucine-rich repeat kinase family, v-yes-1 Yamaguchi sarcoma viral related oncogene homolog (LYN), male germ cell-associated kinase (MAK), MAP/microtubule affinity-regulating kinase family, microtubule associated serineithreonine kinase family, maternal embryonic leucine zipper kinase, c-mer proto-oncogene tyrosine kinase (MERTK), met proto-oncogene (hepatocyte growth factor receptor), MAP kinase interacting serineithreonine kinase family, myosin light chain kinase family, mixed lineage kinase domain-like protein isoform, CDC42 binding protein kinase family, serineithreonine kinase family, macrophage stimulating 1 receptor (c-met-related tyrosine kinase) (MST1R), mechanistic target of rapamycin (serine/threonine kinase) (MTOR), muscle-skeletal-receptor tyrosine kinase (MUSK), myosin light chain kinase family, NIMA (never in mitosis gene a)-related kinase family, serineithreonine-protein kinase NIM1 (NIM1), nemo-like kinase (NLK), oxidative-stress responsive 1 (OSR1), p21 protein (Cdc42/Rac)-activated kinase family. PAS domain containing serineithreonine kinase, Platelet-derived growth factor receptor family, 3-phosphoinositide dependent protein kinase-1 (PDPK1), Calcium-dependent protein kinase 1, phosphorylase kinase gamma family, Phosphatidylinositol 4,5-bisphosphate 3-kinase, phosphoinositide-3-kinase family, phosphatidylinositol 4-kinase family, phosphoinositide kinase, FYVE finger containing, Pim-1 oncogene (PIM1), pim-2 oncogene (PIM2), pim-3 oncogene (PIM3), phosphatidylinositol-4-phosphate 5-kinase family, phosphatidylinositol-5-phosphate 4-kinase family protein kinase, membrane associated tyrosinelthreonine 1 (PKMYT1), protein kinase N family, polo-like kinase family, protein kinase C family, protein kinase D family, cGMP-dependent protein kinase family, eukaryotic translation initiation factor 2-alpha kinase 2 (PRKR), X-linked protein kinase (PRKX), Prolactin receptor (PRLR), PRP4 pre-mRNA processing factor 4 homolog B (yeast) (PRP4), PTK2B protein tyrosine kinase 2 beta (PTK2B), SIK family kinase 3 (QSK), v-raf-1 murine leukemia viral oncogene homolog 1 (RAF1), Neurotrophic tyrosine kinase receptor type family, receptor (TNFRSF)-interacting serine-threonine kinase family, dual serineithreonine and tyrosine protein kinase (RIPK5), Rho-associated, coiled-coil containing, protein, kinase family, c-ros oncogene 1, receptor tyrosine kinase (ROS1), ribosomal protein S6 kinase family, SH3-binding domain kinase 1 (SBK1), serumiglucocorticoid regulated kinase family, Putative uncharacterized serineithreonine-protein kinase (Sugen kinase 110) (SgK110), salt-inducible kinase family, SNF related kinase (SNRK), src-related kinase, SFRS protein kinase family, Spleen tyrosine kinase (SYK), TAO kinase family TANK-binding kinase 1 (TBK1), tec protein tyrosine kinase (TEC), testis-specific kinase 1 (TESK1), transforming growth factor, beta receptor family, tyrosine kinase with immunoglobulin-like and EGF-like domains 1 (TIE1), TEK tyrosine kinase, endothelial (TIE2), Angiopoietin-1 receptor (Tie2), tousled-like kinase family, TRAF2 and NCK interacting, kinase (TNIK), non-receptor tyrosine kinase family, TNNI3 interacting kinase (TNNI3K), transient receptor potential cation channel, testis-specific serine kinase family, TTK protein kinase (TTK), TXK tyrosine kinase (TXK), Tyrosine kinase 2 (TYK2), TYRO3 protein tyrosine kinase (TYRO3), unc-51-like kinase family, phosphatidylinositol 3-kinase, vaccinia related kinase 2 (VRK2), WEE1 homolog family, VVNK lysine deficient protein kinase family, v-yes-1 Yamaguchi sarcoma viral oncogene homolog 1 (YES), sterile alpha motif and leucine zipper containing kinase AZK (ZAK), zeta-chain (TCR) associated protein kinase 70 kDa (ZAP70); Examples of nuclear hormone receptors include but are not limited to: Androgen receptor (AR), Estrogen related receptor alpha (ESRRA), Estrogen receptor 1 (ESR1), Nuclear receptor subfamily 1-group H-member 4 (NR1H4), Nuclear receptor subfamily 3-group C-member 1 (glucocorticoid receptor) (NR3C1), Nuclear receptor subfamily 1-group H-member 3 (Liver X receptor α) (NR1H3), Nuclear receptor subfamily 1-group H-member 2 (Liver X receptor β) (NR1H2), Nuclear receptor subfamily 1-group H-member 2 (Liver X receptor β) (NR1H2), Nuclear receptor subfamily 3-group C-member 2 (Mineralcorticoid receptor) (NR3C2), Peroxisome Proliferator Activated Receptor alpha (PPARA), Peroxisome Proliferator Activated Receptor gamma (PPARG), Peroxisome Proliferator Activated Receptor delta (PPARD), Progesterone receptor α (PGR), Progesterone receptor β (PGR), Retinoic acid receptor-alpha (RARA), Retinoic acid receptor-beta (RARE), Retinoid X receptor-alpha (RXRA), Retinoid X receptor-gamma (RXRG), Thyroid hormone receptor-alpha (THRA), Thyroid hormone receptor-beta (THRB), Retinoic acid-related orphan receptor, Liver X receptor, Farnesoid X receptor, Vitamin D receptor, Pregnane X receptor, Constitutive androstane receptor, Hepatocyte nuclear factor 4, Oestrogen receptor, Oestrogen-related receptor, Glucocortioic receptor, Nerve growth factor-induced-B, Germ cell nuclear factor; Examples of Epigenetic targets include but are not limited to: ATPase family AAA domain-containing protein 2 (ATAD2A), ATPase family-AAA domain containing 2B (ATAD2B), ATPase family AAA domain containing-2B (ATAD2B), bromodomain adjacent to zinc finger domain-1A (BAZ1A), bromodomain adjacent to zinc finger domain-1B (BAZ1B), bromodomain adjacent to zinc finger domain-2A (BAZ2A), bromodomain adjacent to zinc finger domain-2A (BAZ2A), bromodomain adjacent to zinc finger domain-2B (BAZ2B), bromodomain-containing protein 1 (BRD1), Bromodomain containing protein 2-1 st bromodomain (BRD2), Bromodomain containing protein 2-1 st & 2 nd bromodomains (BRD2), bromodomain-containing protein 2 isoform 1-bromodomain 2 (BRD2(2)), bromodomain-containing protein 3-bromodomain 1 (BRD3(1)), Bromodomain-containing protein 3-1 st bromodomain (BRD3), Bromodomain-containing protein 3-1 st & 2 nd bromodomains (BRD3), bromodomain-containing protein 3-bromodomain 2 (BRD3(2)), Bromodomain containing protein 4-1 st bromodomain (BRD4), bromodomain-containing protein 4 isoform long-bromodomains 1 and 2 (BRD4(1-2)), bromodomain-containing protein 4 isoform long-bromodomain 2 (BRD4(2)), bromodomain-containing protein 4 isoform short (BRD4(full-length-short-iso.)), Bromodomain containing protein 7 (BRD7), bromodomain containing 8-bromodomain 1 (BRD8(1)), bromodomain containing 8-bromodomain 2 (BRD8(2)), bromodomain-containing protein 9 isoform 1 (BRD9), Bromodomain containing testis-specific-1 st bromodomain (BRDT), Bromodomain containing testis-specific-1st & 2nd bromodomains (BRDT), bromodomain testis-specific protein isoform b-bromodomain 2 (BRDT(2)), bromodomain and PHD finger containing-1 (BRPF1), bromodomain and PHD finger containing-3 (BRPF3), bromodomain and PHD finger containing-3 (BRPF3), Bromodomain and WD repeat-containing 3-2 nd bromodomain (BRWD3(2)), Cat eye syndrome critical region protein 2 (CECR2), CREB binding protein (CREBBP) E1A binding protein p300 (EP300), EP300 (EP300), nucleosome-remodeling factor subunit BPTF isoform 1 (FALZ), Nucleosome-remodeling factor subunit BPT (FALZ), Euchromatic histone-lysine N-methyltransferase 2 (EHMT2), Histone Acetyltransferase-KAT2A (GCN5L2), Euchromatic histone-iysine N-methyltransferase 1 (EHMT1), Histone-lysine N-methyltransferase MLL (MLL), Polybromo 1-1 st bromodomain (PB1(1)), Polybromo 1-2 nd bromodomain (PB1(2)), polybromo 1-bromodomain 2 (PBRM1(2)), polybromo 1-bromodomain 5 (PBRM1(5)), Histone acetyltransferase KAT2B (PCAF), PH-interacting protein-1 st bromodomain (PHIP(1)), PH-interacting protein-2 nd bromodomain (PHIP (2)), Protein kinase C-binding protein 1 (PRKCBP1), Protein arginine N-methyltransferase 3 (PRMT3), SWI/SNF related-matrix associated-actin dependent regulator of chromatin-subfamily a-member 2 (SMARCA2), SWI/SNF related-matrix associated-actin dependent regulator of chromatin-subfamily a-member 4 (SMARCA4), Nuclear body protein-SP110 (SP110), Nuclear body protein-SP140 (SP140), Transcription initiation factor TFIID subunit 1 (TAF1(1-2)), TAF1 RNA polymerase II-TATA box binding protein (TBP)-associated factor-250 kDa bromodomain 2 (TAF1(2)), Transcription initiation factor TFIID subunit 1-like-1 st bromodomain (TAF1L(1)), Transcription initiation factor TF110 subunit 1-like-2 nd bromodomain (TAF1L (2)), tripartite motif containing 24 (TRIM24(Bromo.)), tripartite motif containing 24 (TRIM24(PHD-Bromo.)), E3 ubiquitin-protein ligase TRIM33 (TRIM33), tripartite motif containing 33 (TRIM33(PHD-Bromo.)), WD repeat 9-1 st bromodomain (WDR9(1)), WD repeat 9-2 nd bromodomain (WDR9(2)); membrane transport proteins including but not limited to ATP-binding cassette (ABC) superfamily, solute carrier (SLC) superfamily, multidrug resistance protein 1 (P-glycoprotein), organic anion transporter 1, and protein such as EAAT3, EAAC1, EAAT1, GLUT1, GLUT2, GLUT9, GLUT10, rBAT, AE1, NBC1, KNBC, CHED2, BTR1, NABC1, CDPD, SGLT1, SGLT2, NIS, CHT1, NET, DAT, GLYT2, CRTR, B0AT1, SIT1, XT3, y+LAT1, BAT1, NHERF1, NHE6, ASBT, DMT1, DCT1, NRAMP2, NKCC2, NCC, KCC3, NACT, MCT1, MCT8, MCT12, SLD, VGLUT3, THTR1, THTR2, PIT2, GLVR2, OCTN2, URAT1, NCKX1, NCKX5, CIC, PiC, ANT1, ORNT1, AGC1, ARALAR, Citrin, STL2, aralar2, TPC, MUP1, MCPHA, CACT, GC1, PHC, DTD, CLD, DRA, PDS, Prestin, TAT1, FATP4, ENT3, ZnT2, ZnT10, AT1, NPT2A, NPT2B, HHRH, CST, CDG2F, UGAT, UGTL, UGALT, UGT1, UGT2, FUCT1, CDG2C, NST, PAT2, G6PT1, SPX4, ZIP4, LIV4, ZIP13, LZT-Hs9, FPN1, MTP1, IREG1, RHAG, AIM1, PCFT, FLVCR1, FLVCR2, RFT1, RFT2, RFT3, OATP1B1, OATP1B3, OATP2A1; structural proteins including but not limited to tubulin, heat shock protein, Microtubule stabilizing proteins, Oncoprotein 18, stathmin, kinesin-8 and kinesin-14 family, Kip3, Kif18A, proteases including but not limited ADAM (a disintegrin and metalloprotease) family; Other molecule targets in signal transductions include but are not limited to: Cell division cycle 25 homolog A (CDC25A), forkhead box O3 (forkhead box O3), nuclear factor of kappa light polypeptide gene enhancer in B-cells inhibitor, alpha (NFKBIA), nuclear factor (erythroid-derived 2)-like 2 (NFE2L2), Natriuretic peptide receptor A (NPR1) Tumor necrosis factor receptor superfamily, member 11a (TNFRSF11A), v-rel reticuroendotheliosis viral oncogene homolog A (avian) (RELA), Sterol regulatory element binding transcription factor 2 (SREBF2), CREB regulated transcription coactivator 1 (CRTC1), CREB regulated transcription coactivator 2 (CRTC2), X-box binding protein 1 (XBP1), Catenin (cadherin-associated protein), beta 1 (CTNNB1), and combinations thereof.

Examples of known biologics include but are not limited to: Abbosynagis, Abegrin, Acterrira, AFP-Cide, Antova, Arzerra, Aurexis, Avastin, Benlysta, Bexxar, Blontress, Bosatria, Campath, CEA-fide, CEA-Scan, Cimzia, Cyramza, Ektoniab, Erbitux, FbriScint, Gazyva, Herceptin, hPAM4-Cide, HumaSPECT, HuMax-CD4, HuMax-EGFr, Humira, HuZAF, Hybri-ceaker, Bans, Indimacis-125, Kadcyla, Lemtrada, LeukArrest, LeukoScan, Lucentis, Lymphomun, LymphoScan, LymphoStat-B, MabThera, IViycograb, Mylotarg, Myoscint, NeutroSpec, Numax, Nuvion, Omnitarg, Opdivo, Orthoclone OKT3, OvaRex, Panorex, Prolia, Prostascint, Raptiva, Remicade, Removab, Rencarex, ReoPro, Rexomun, Rituxan, RoActemra, Scintimun, Simponi, Simulect, Soliris, Steiara, Synagis, Tactress, Theracim, Theragyn, Theraloc, Tysabri, Vectibix, Verluma, Xolair, Yervoy, Zenapax, and Zevalin or combinations thereof.

Examples of known Monoclonal antibodies include but are not limited to: 3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pegol, ALD518, ALD403, Alemtuzumab, Alirocumab, Altumomab pentetate, Amatuximab, AMC 334, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab, Atorolimumab, Aveiumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrutnab, Bitnekizumab, Bivatuzumab mertansine, Bleselumab, Blinatumomab, Blontuvetmab, Blosozumab, Bococizumab, Brazikumab, Brentuximab vedotin, Briakinumab, Brodalumab, Brducizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapindizumab pegol, Daratumumab, Dectrekumab, Demcizumab, Der intuzumab mafodotin, Denosumab, Depatuxizumab mafodotin, Derlotuximab biotin, Detumomab, Dinutuximab, Diriclavumab, Domagrozumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Ermbetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fandesomab, Faralimomab, Farletuzumab, Fasinumab, FBTA05, Felvizumab, Fezakinumab, Fibatuzumab, Ficlatuzumab, Figitumumab, Firivumab, Flanvotumab, Fletikumab, Fontolizumab, Foralumab, Foravirurmab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMA-638, IMAB362, Imatumab, Imciromab, imgatuzumab, Inclacumab, Indatuximab ravtansine, Indusatumab vedotin, Inebilizumab, Infliximab, Inotimomab, Inotuzumab ozogamicin, Intetumumab, Ipilimumab, Iratumumab, Isatuximab, Itolizumab, Ixekizumab, Keliximab, Labetuzumab, Lambrolizumab, Lampalizumalo, Lanadelumab, Landogrozumab, Laprituximab emtansine, LBR-101/PF044297429, Lebrikizumab, Lemaiesomab, Leridalizumab, Lenzilumab, Lerdelimumab, Lexatumumab, Libivirumab, Lifastuzumab vedotin, Ligelizumab, Lilotomab satetraxetan, Lintuzumab, Liritumab, Losielcizumab, Lokivetmab, Lorvotuzumab mertansine, Lucatumumab, Lulizumab pegol, Lumifiximab, Lumretuzumab, LY2951742, Mapatumumab, Margetuximab, Maslimomab, Matuzumab, Mavrilimumab, Mepolizumab, Metelimumab, Milatuzumab, Minretumomab, Mirvetuximab soravtansine, Mitumomab, MogamuHzumab, Monalizumab, Mordimumab, Motavizumab, Moxetumomab pasudotox, Muromonab-CD3, Nacdomab tafenatox, Namilumab, Naptumomab estafenatox, Naratuximab emtansine, Namatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otiertuzumab, Oxelumab, Ozanezumab, Ozoralizumab, Pagbaximab, Palivizumab, PamrevIumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Res/izumab, Rilotumumab, Rinucumab, Rsankizumab, Rituximab, Rivabazumab pegol, Robatumumab, Rotedumab, Romosozumab, RontaHzumab, Rovalpituzumab tesirine, Rovelizumab, Ruptizumab, Sacituzumab govitecan, Samalizumab, Sapelizumab, Sarilumab, Satumomab pendetide, Secukinumab, Senbantumab, Setoxaximab, Sevirumab, SGN-CD19A, SGN-CD33A, Sibratuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Teneliximab, Teplizumab, Teprotumumab, Tesicidumab, Tetulomab, Tezepelumab, TGN1412, Ticilimumab, Tigatuzumab, Tildrakizumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, TRBS07, Tregahzumab, Tremefimumab, Trevogrumab, Tucotuzumab celmoleukin, Tuvtrumab, tiblituximab, Ulocuplumab, Urelumab, Urtoxazumab, Ustekinumab, Utomilumab, Vadastuximab talirine, Vandortuzumab veclotin, Vantictumab, Vanucizumab, Vapaliximab, Varlilumab, Vatelizumab, Vedolizumab, Veituzumab, Vepalimomab, Vesencumab, Visilizumab, Vobarilizumab, Volociximab, Vorsetuzumab matodotin, Votumumab, Xentuzumab, Zalutumumab, Zanolimumab, Zatuximab, Ziralimumab, and Zolimomab aritox or combinations thereof.

Examples of vaccines developed for viral diseases include but are not limited to: Hepatitis A vaccine, Hepatitis B vaccine, Hepatitis E vaccine, HPV vaccine, Influenza vaccine, Japanese encephalitis vaccine, MMR vaccine, MMRV vaccine, Polio vaccine, Rabies vaccine, Rotavirus vaccine, Varicella vaccine, Shingles vaccine, Smallpox vaccine, Yellow Fever vaccine, Adenovirus vaccine, Coxsackie B virus vaccine, Cytomegalovirus vaccine, Dengue vaccine for humans, Eastern Equine encephalitis virus vaccine for humans, Ebola vaccine, Enterovirus 71 vaccine, EpsteinBarr vaccine, Hepatitis C vaccine, HIV vaccine, HTLV-1 T-lymphotropic leukemia vaccine for humans, Marburg virus disease vaccine, Norovirus vaccine, Respiratory syncytial virus vaccine for humans, Severe acute respiratory syndrome (SARS) vaccine, West Nile virus vaccine for humans; Examples of bacterial diseases include but are not limited to. Anthrax vaccines, DPT vaccine, Q fever vaccine, Hib vaccine, Tuberculosis (BCG) vaccine, Meningococcal vaccine, Typhoid vaccine, Pneumococcal conjugate vaccine, Pneumococcal polysaccharide vaccine, Cholera vaccine, Caries vaccine, Ehrlichlosis vaccine, Leprosy vaccine, Lyme disease vaccine, *Staphylococcus aureus* vaccine, *Streptococcus pyogenes* vaccine, *Syphilis* vaccine, *Tularemia* vaccine, *Yersinia pestis* vaccine; Examples of parasitic diseases include but are not limited to: Malaria vaccine, Schistosomiasis vaccine, Chagas disease vaccine, Hookworm vaccine, Onchocerciasis river blindness vaccine for humans, Trypanosomiasis vaccine, Visceral leishmaniasis vaccine; Examples of non-infectious diseases include but are not limited to: Alzheimer's disease amyloid protein vaccine, Breast cancer vaccine, Ovarian cancer vaccine, Prostate cancer vaccine, Talimogene laherparepvec (T-VEC); also vaccines including but not limited to the following trade names: ACAM2000, ActHIB, Adacel, Muria, AFLURIA QUADRIVALENT, Agriflu, BCG Vaccine, BEXSERO, Biothrax, Boostrix, Cervarix, Comvax, DAPTACEL, DECAVAC, Engerix-B, FLUAD, Fluarix, Fluarix Quadrivalent, Flublok, Flucelvax, Fluceivax Quadrivalent, FluLaval, FluMist, FluMist Quadrivalent, Fluvirin, Fluzone Quadrivalent, Fluzone, Fluzone High-Dose and Fiuzone Intradermal, Gardasil, Gardasil 9, Havrix, Hiberix, Imovax, Infanrix, IPOL, Ixiaro, JE-Vax, KINRIX, Menactra, Men-Hibrix, Menomune-A/C/Y/W-135, Menveo, M-M-R II, M-M-Vax, Pediarix, PedvaxHIB, Pentacel, Pneumovax 23, Poliovax, Prevnar, Prevnar 13, ProQuad, Quadracel, Quadrivalent, RabAvert, Recombivax HB, ROTARIX, RotaTeq, TENIVAC, TICE BCG, Tripeclia, TRUMENBA, Twinrix, TYPHIM Vi, VAQTA, Varivax, Vaxchora, Vivotif, YF-Vax, Zostavax, and combinations thereof.

Examples of injectable drugs include but are not limited to: Ablavar (Gadofosveset Trisoclium Injection), Abarelix Depot, Abobotulinumtoxin A injection (Dysport), ABT-263, ABT-869, ABX-EFG, Accretropin (Somatropin Injection), Acetadote (Acetylcysteine Injection), Acetazolamide Injection (Acetazolamide Injection), Acetylcysteine Injection (Acetadote), Actemra (Tocilizumab injection), Acthrel (Corticorelin Ovine Triflutate for injection), Actummune, Activase, Acyclovir for Injection (Zovirax Injection), [0137], Adacel, Adalimumab, Adenoscan (Adenosine Injection), Adenosine Injection (Adenoscan), Adrenaclick, AdreView (Iobenguane 1123 Injection for Intravenous Use), Afluria, Ak-Fluor (Fluorescein Injection), Aldurazyme (Laronidase), Alglucerase Injection (Ceredase), Alkeran Injection (Melphalan Hcl injection), Allopurinol Sodium for Injection (Aloprim), Aloprim (Allopurinol Sodium for Injection), Alprostadil, Alsuma (Sumatriptan Injection), ALTU-238, Amino Acid injections, Aminosyn, Apidra, Apremilast, Alprostadil Dual Chamber System for Injection (Caverject Impulse), AMG 009, AMG 076, AMG 102, AMG 108, AMG 114, AMG 162, AMG 220, AMG 221, AMG 222, AMG 223, AMG 317, AMG 379, AMG 386, AMG 403, AMG 477, AMG 479, AMG 517, AMG 531, AMG 557, AMG 623, AMG 655, AMG 706, AMG 714, AMG 745, AMG 785, AMG 811, AMG 827, AMG 837, AMG 853, AMG 951, Amiodarone HCl Injection (Amiodarone HCl Injection), Amobarbital Sodium Injection (Amytal Sodium), Amytal Sodium (Amobarbital Sodium Injection), Anakinra, Anti-Abets, Anti-Beta7, Anti-Beta20 Anti-CD4, Anti-D23; Anti-CD40, Anti-IFNalpha, Anti-IL13, Anti-OX40L, Anti-ox-LDS, Anti-NGF, Anti-NRP1, Arixtra. Amphadase (Hyaluronidase Inj), Ammonul (Sodium Phenylacetate and Sodium Benzoate injection), Anaprox, Anzemet Injection (Doiasetron Mesylate Injection), Apidra (Insulin Glulisine [rDNA origin] Inj), Apomab, Aranesp (darbepoetin alfa), Argatroban (Argatroban injection), Arginine Hydrochloride Injection (R-Gene 10, Aristocort, Aristospan, Arsenic Trioxide injection (Trisenox), Articane HCl and Epinephrine Injection (Septocaine), Arzerra (Ofatumumab Injection), Asciera (Polidocanol Injection), Ataluren, Ataluren-DMD, Atenolol Inj (Tenormin I.V. Injection), Atracurium Besylate Injection (Atracurium Besylate Injection), Avastin, Azactam Injection (Aztreonam Injection), Azithromycin (Zithromax Injection), Aztreonam Injection (Azactam Injection), Baclofen Injection (Lioresal Intrathecal), Bacteriostatic Water (Bacteriostatic Water for Injection), Baclofen Injection (Lioresal Intrathecal), Bal in Oil Ampules (Dimercarprol Injection), BayHepB, BayTet, Benadryl, Bendamustine Hydrochloride Injection (Treanda), Benztropine Mesylate Injection (Cogentin), Betamethasone Injectable Suspension (Celestone Soluspan), Bexxar, Bicillin C-R 900/300 (Penicillin G Benzathine and Penicillin G Procaine Injection), Blenoxane (Bleomycin Sulfate Injection), Bleomycin Sulfate Injection (Blenoxane), Boniva Injection (Ibandronate Sodium Injection), Botox Cosmetic (OnabotulinumtoxinA for Injection), BR3-FC, Bravelle (Urofollitropin Injection), Bretylium (Bretylium Tosylate Injection), Brevital Sodium (Methohexital Sodium for Injection), Brethine, Briobacept, BTT-1023, Bupivacaine HCl, Byetta, Ca-DTPA (Pentetate Calcium Trisoclium Inj), Cabazitaxel Injection (Jevtana), Caffeine Alkaloid (Caffeine and Sodium Benzoate Injection), Calcijex Injection (Calcitrol), Calcitrol (Calcijex Injection), Calcium Chloride (Calcium Chloride Injection 10%), Calcium Disodium Versenate (Edetate Calcium Disodium Injection), Campath (Altemtuzumab), Camptosar Injection (Irinotecan Hydrochloride), Canakinumab Injection (Ilaris), Capastat Sulfate (Capreomycin for Injection), Capreomycin for Injection (Capastat Sulfate), Cardiolite (Prep kit for Technetium Tc99 Sestamibi for Injection), Carticel, Cathflo, Cefazolin and Dextrose for Injection (Cefazolin Injection), Cefepime Hydrochloride, Cefotaxime, Ceftriaxone, Cerezyme, Carnitor Injection, Caverject, Celestone Soluspan, Celsior, Cerebyx (Fosphenytoin Sodium Injection), Ceredase (Alglucerase Injection), Ceretec (Technetium Tc99m Exametazime Injection), Certolizumab, CF-101, Chloramphenicol Sodium Succinate (Chloramphenicol Sodium Succinate Injection), Chloramphenicol Sodium Succinate Injection (Chloramphenicol Sodium Succinate), Cholestagel (Colesevelam HCL), Choriogonadotropin Alfa Injection (Ovidrel), Cimzia, Cisplatin (Cisplatin Injection), Clolar (Clofarabine Injection), Clomiphine Citrate, Clonidine injection (Duraclon), Cogentin (Benztropine Mesylate Injection), Colistimethate injection (Coly-Mycin M), Coly-Mycin M (Colistimethate Injection), Compath, Conivaptan Hcl Injection (Vaprisol), Conjugated Estrogens for Injection (Premarin Injection), Copaxone, Corticorelin Ovine Triflutate for Injection (Acthrel), Corvert (Ibutilide Fumarate Injection), Cubicin (Daptomycin injection), CF-101, Cyanokit (Hydroxocobalamin for Injection), Cytarabine Liposome Injection (DepoCyt), Cyanocobalamin, Cytovene (ganciclovir), D.H.E. 45, Dacetuzumab, Dacogen (Decitabine Injection), Dalteparin, Dantrium IV (Dantrolene Sodium for Injection), Dantrolene Sodium for Injection (Dantrium IV), Daptomycin Injection (Cubicin), Darbepoietin Alfa, DDAVP Injection (Desmopressin Acetate Injection), Decavax, Decitabine Injection (Dacogen), Dehydrated Alcohol (Dehydrated Alcohol Injection), Denosumab Injection (Prolia), Delatestryl, Delestrogen, Delteparin Sodium, Depacon (Valproate Sodium Injection), Depo Medrol (Methylprednisolone Acetate Injectable Suspension), Depo-Cyt (Cytarabine Liposome Injection), DepoDur (Morphine Sulfate XR Liposome Injection), Desmopressin Acetate Injection (DDAVP Injection), Depo-Estradioi, Depo-Provera 104 mg/ml, Depo-Provera 150 mg/ml, Depo-Testosterone, Dexrazoxane for Injection, Intravenous Infusion Only (Totect), Dextrose/Electrolytes, Dextrose and Sodium Chloride Inj (Dextrose 5% in 0.9% Sodium Chloride), Dextrose, Diazepam Injection (Diazepam Injection), Digoxin Injection (Lanoxin Injection), Dilaudid-HP (Hydromorphone Hydrochloride Injection), Dimercarprol Injection (Bal in Oil Ampules), Diphenhydramine Injection (Benadryl Injection), Dipyridamole Injection (Dipyridamole Injection), DMOAD, Docetaxel for Injection (Taxotere), Dolasetron Mesylate Injection (Anzemet Injection), Doribax (Doripenem for Injection), Doripenem for Injection (Doribax), Doxercalciferol Injection (Hectorol Injection), Doxil (Doxorubicin Hcl Liposome Injection), Doxorubicin Hcl Liposome Injection (Doxil), Duraclon (Clonidine Injection), Duramorph (Morphine Injection), Dysport (Abobotulinumtoxin A Injection), Ecallantide Injection (Kalbitor), EC-Naprosyn (naproxen), Edetate Calcium Disodium Injection (Calcium Disodium Versenate), Edex (Alprostadil for Injection), Engerix, Edrophonium Injection (Enlon), Eligiustat Tartate, Eloxatin (Oxaliplatin Injection), Emend Injection (Fosaprepitant Dimeglumine Injection), Enalaprilat Injection (Enalaprilat Injection), Enlon (Edrophonium Injection), Enoxaparin Sodium Injection (Lovenox), Eovist (Gadoxetate Disodium Injection), Enbrel (etanercept), Enoxaparin, Epicel, Epinepherine, Epipen, Epipen Jr., Epratuzumab, Erbitux, Ertapenem Injection (Invanz), Erythropoieten, Essential Amino Acid Injection (Nephramine), Estradiol Cypionate, Estradiol Valerate, Etanercept, Exenatide Injection (Byetta). Evlotra, Fabrazyme (Adalsidase beta), Famotidine Injection, FDG (Fludeoxyglucose F 18 Injection), Feraheme (Ferumoxytol Injection), Feridex I.V. (Ferumoxides Injectable Solution), Fertinex, Ferumoxides Injectable Solution (Feridex I.V.), Ferumoxytol Injection (Feraheme), Fiagyl Injection (Metronidazole Injection), Fluarix, Fludara (Fludarabine Phosphate), Fludeoxyglucose F 18 Injection (FDG), Fluorescein Injection (Ak-Fluor), Foilistim AQ Cartridge (Follitropin Beta Injection), Follitropin Alfa Injection (Gonal-f RFF), Follitropin Beta Injection (Follistim AQ Cartridge), Folotyn (Praiatrexate Solution for Intravenous Injection), Fonclaparinux, Forteo (Teriparatide (rDNA origin) Injection), Fostamatinib, Fosaprepitant Dimegiumine Injection (Emend Injection), Foscamet Sodium Injection (Foscavir), Foscavir (Foscamet Sodium Injection), Fosphenytoin Sodium Injection (Cerebyx), Fospropofol Disodium Injection (Luseclra), Fragmin, Fuzeon (enfuvirtide), GA101, Gadobenate Dimeglumine Injection (Multihance), Gadofosveset Trisodium Injection (Ablavar), Gadoteridol Injection Solution (ProHance), Gadoversetamide Injection (OptiMARK), Gadoxetate Disoclium Injection (Eovist), Ganirelix (Ganirelix Acetate injection), Gardasil, GC1008, GDFD, Gemtuzumab Ozogamicin for Injection (Mylotarg), Genotropin, Gentamicin Injection, GENZ-112638, Golimumab Injection (Simponi Injection), Gonal-f RFF (Follitropin Alfa Injection), Granisetron Hydrochloride (Kytril Injection), Gentamicin Sulfate, Glatirarrier Acetate, Glucagen, Glucagon, HAE1, Haldol (Haloperidol Injection), Havrix, Hectorol Injection (Doxercalciferol Injection), Hedgehog Pathway Inhibitor, Heparin, Herceptin, hG-CSF, Humelog, Human Growth Hormone, Humatrope, HuMax, Humegon, Humira, Humulin, Ibandronate Sodium Injection (Boniva Injection), Ibuprofen Lysine Injection (NeoProfen), Ibutilide Fumarate Injection (Corvert), Idamycin PFS (Idarubicin Hydrochloride Injection), Idarubicin Hydrochloride Injection (Idamycin PFS), Marls (Canakinumab Injection), Imipenem and Cilastatin for Injection (Primaxin I.V.), Imitrex, Incobotulinumtoxin A for Injection (Xeomin), Increlex (Mecasermin [rDNA origin] Injection), Indocin IV (Indomethacin Inj), Indomethacin Inj (Indocin IV), infanrix, Innohep, Insulin, Insulin Aspart [rDNA origin] Inj (NovoLog), Insulin Glargine [rDNA origin] Injection (Lantus), Insulin Glulisine [rDNA origin] Inj (Apidra), Interferon alfa-2b, Recombinant for Injection (Intron A), Intron A (Interferon alfa-2b, Recombinant for Injection), Invanz (Ertapenem Injection), Invega Sustenna (Paliperidone Palmitate Extended-Release Injectable Suspension), Invirase (saquinavir mesylate), Iobenguane 1123 Injection for Intravenous Use (AdreView), Iopromide injection (Ultravist), Ioversol Injection (Optiray Injection), Iplex (Mecasermin Rinfabate [rDNA origin] Injection), Iprivask, Irinotecari Hydrochloride (Camptosar Injection), Iron Sucrose Injection (Venofer), Istodax (Romidepsin for Injection), Itraconazole Injection (Sporanox Injection), Jevtana (Cabazitaxel Injection), Jonexa, Kalbitor (Ecallantide Injection), KCL in D5NS (Potassium Chloride in 5% Dextrose and Sodium Chloride Injection), KCL in D5W, KCL in NS, Kenalog 10 Injection (Triamcinolone Acetonide Injectable Suspension), Kepivance (Palifermin), Keppra Injection (Levetiracetam), Keratinocyte, KFG, Kinase Inhibitor, Kineret (Anakinra), Kinlytic (Urokinase Injection), Kinrix, Klonopin (clonazepam), Kytril Injection (Granisetron Hydrochloride), Iacosamide Tablet and Injection (Vimpat), Lactated Ringer's, Lanoxin Injection (Digoxin Injection), Lansoprazole for Injection (Prevacid I.V.), Lantus, Leucovorin Calcium (Leucovorin Calcium Injection), Lente (L), Leptin, Levemir, Leukine Sargramostim, Leuprolide Acetate, Levothyroxine, Levetiracetam (Keppra Injection), Lovenox, Levocarnitine Injection (Carnitor Injection), Lexiscan (Regadenoson Injection), Lioresal Intrathecal (Baclofen Injection), Liraglutide [rDNA] Injection (Victoza), Lovenox (Enoxaparin Sodium Injection), Lucentis (Ranibizumab Injection), Lumizyme, Lupron (Leuprolide Acetate Injection), Lusedra (Fospropofol Disodium Injection), Maci, Magnesium Sulfate (Magnesium Sulfate Injection), Mannitol Injection (Mannitol IV), Marcaine (Bupivacaine Hydrochloride and Epinephrine Injection), Maxipime (Cefepime Hydrochloride for Injection), MDP Multidose Kit of Technetium Injection (Technetium Tc99m Medronate Injection), Mecasermin [rDNA origin] Injection (Increlex), Mecasermin Rinfabate [rDNA origin] Injection (Iplex), Melphalan Hcl Injection (Alkeran Injection), Methotrexate, Menactra, Menopur (Menotropins Injection), Menotropins for injection (Repronex), Methohexital Sodium for injection (Brevital Sodium), Methyidopate Hydrochloride Injection, Solution (Methyldopate Hcl), Methylene Blue (Methylene Blue Injection), Methylprednisolone Acetate Injectable Suspension (Depo Medrol), Met-Mab, Metoclopramide Injection (Reglan Injection), Metrodin (Urofollitropin for Injection), Metronidazole Injection (Flagyl Injection), Miacalcin, Midazolam (Midazolam Injection), Mimpara (Cinacalet), Minocin Injection (Minocycline Inj), Minocycline Inj (Minocin Injection), Mipomersen, Mitoxantrone for Injection Concentrate (Novantrone), Morphine Injection (Duramorph), Morphine Sulfate XR Liposome Injection (DepoDur), Morrhuate Sodium (Morrhuate Sodium injection), Motesanib, Mozobil (Plerixafor Injection), Multihance (Gadobenate Dimeglumine Injection), Multiple Electrolytes and Dextrose Injection, Multiple Electrolytes Injection, Mylotarg (Gemtuzumab Ozogamicin for Injection), Myozyme (Alglucosidase alfa), Nafcillin Injection (Nafcillin Sodium), Nafcillin Sodium (Nafcillin Injection), Naltrexone XR (Vivitrol), Naprosyn (naproxen), NeoProfen (Ibuprofen Lysine Injection), Nandrol Decarioate, Neostigmine Methylsulfate (Neostigmine Methylsulfate Injection), NEO-GAA, NeoTect (Technetium Tc99m Depreoticle Injection), Nephramine (Essential Amino Acid Injection), Neulasta (pegfilgrastim), Neupogen (Filgrastim), Novolin, Novolog, NeoRecormon, Neutrexin (Trimetrexate Glucuronate Inj), NPH (N), Nexterone (Amiodarone HCl Injection), Norditropin (Somatropin Injection), Normal Saline (Sodium Chloride Injection), Novantrone (Mitoxantrone for Injection Concentrate), Novolin 70/30 Innolet (70% NPH, Human Insulin Isophane Suspension and 30% Regular, Human Insulin Injection), NovoLog (Insulin Aspart [rDNA origin] Inj), Nplate (romiplostim), Nutropin (Somatropin (rDNA origin) for Inj), Nutropin AQ, Nutropin Depot (Somatropin (rDNA origin) for Inj), Octreotide Acetate Injection (Sandostatin LAR), Ocrelizumab, Ofatumumab Injection (Arzerra), Olanzapine Extended Release Injectable Suspension (Zyprexa Relprevv), Omnitarg, Omnitrope (Somatropin [rDNA origin] Injection), Ondansetron Hydrochloride Injection (Zofran Injection), OptiMARK (Gadoversetamide Injection), Optiray Injection (Ioversol Injection), Orencia, Osmitrol Injection in Aviva (Mannitol Injection in Aviva Plastic Vessel 250), Osmitrol Injection in Viaflex (Mannitol Injection in Viaflex Plastic Vessel 250), Osteoprotegrin, Ovidrel (Choriogonadotropin Alfa Injection), Oxacillin (Oxacillin for Injection), Oxaliplatin Injection (Eloxatin), Oxytocin Injection (Pitocin), Paliperidone Palmitate Extended-Release Injectable Suspension (Invega Sustenna), Pamidronate Disodium Injection (Pamidronate Disodium Injection), Panitumumab Injection for Intravenous Use (Vectitaix), Papaverine Hydrochloride Injection (Papaverine Injection), Papaverine Injection (Papaverine Hydrochloride Injection), Parathyroid Hormone, Paricalcitol Injection Fliptop Vial (Zemplar Injection), PARP Inhibitor, Pediarix, PEGIntron, Peginterferon, Pegfilgrastim, Penicillin G Benzathine and Penicillin G Procaine, Pentetate Calcium Trisodium Inj (Ca-DTPA), Pentetate Zinc Trisodium Injection (Zn-DTPA), Pepcid Injection (Famotidine Injection), Pergonal, Pertuzumab, Phentolamine Mesylate (Phentolamine Mesylate for Injection), Physostigmine Salicylate (Physostigmine Salicylate (injection)), Physostigmine Salicylate (injection) (Physostigmine Salicylate), Piperacillin and Tazobactam Injection (Zosyn), Pitocin (Oxytocin Injection), Piasma-Lyte 148 (Multiple Electrolytes Inj), Plasma-Lyte 56 and Dextrose (Multiple Electrolytes and Dextrose Injection in Viaflex, Plastic Vessel 250), PlasmaLyte, Plerixafor Injection (Mozobil), Polidocanol Injection (Aselera), Potassium Chloride, Pralatrexate Solution for Intravenous Injection (Folotyn), Pramlintide Acetate Injection (Symlin), Premarin Injection (Conjugated Estrogens for Injection), Prep kit for Technetium Tc99 Sestamibi for Injection (Cardiolite), Prevacid I.V. (Lansoprazole for Injection), Primaxin I.V. (Imipenem and Cilastatin for Injection), Prochymal, Procrit, Progesterone, ProHance (Gadoteridol Injection Solution), Prolia (Denosumab Injection), Promethazine HCl Injection (Promethazine Hydrochloride Injection), Propranolol Hydrochloride Injection (Propranolol Hydrochloride Injection), Quinidine Gluconate Injection (Quinidine Injection), Quinidine Injection (Quinidine Gluconate Injection), R-Gene 10 (Arginine Hydrochloride Injection), Ranibizumab Injection (Lucentis), Ranitidine Hydrochloride Injection (Zantac Injection), Raptiva, Reclast (Zoledronic Acid Injection), Recombivarix HB, Regadenoson Injection (Lexiscan), Reglan Injection (Metoclopramide Injection), Remicade, Renagel, Renvela (Sevelamer Carbonate), Repronex (Menotropins for Injection), Retrovir IV (Zidovudine Injection), rhApo2L/TRAIL, Ringer's and 5% Dextrose Injection (Ringers in Dextrose), Ringer's Injection (Ringers Injection), Rituxan, Rituximab, Rocephin (ceftriaxone), Rocuronium Bromide Injection (Zemuron), Roferon-A (interferon alfa-2a), Romazicon (flumazenil), Romidepsin for Injection (Isodax), Saizen (Somatropin Injection), Sandostatin LAR (Octreotide Acetate Injection), Scierostin Ab, Sensipar (cinacalcet), Sensorcaine (Bupivacaine HCl Injections), Septocaine (Art cane HCl and Epinephrine Injection), Serostim LQ (Somatropin (rDNA origin) Injection), Simponi Injection (Golimumab Injection), Sodium Acetate (Sodium Acetate Injection), Sodium Bicarbonate (Sodium Bicarbonate 5% Injection), Sodium Lactate (Sodium Lactate Injection in AVIVA), Sodium Phenylacetate and Sodium Benzoate Injection (Ammonul), Somatropin (rDNA origin) for Inj (Nutropin), Sporanox injection (Itraconazole Injection), Stelara Injection (Ustekinumab), Stemgen, Sufenta (Sufentanil Citrate Injection), Sufentanil Citrate Injection (Sufenta), Sumavel, Sumatriptan Injection (Alsuma), Symlin, Symlin Pen, Systemic Hedgehog Antagonist, Synvisc-One (Hylan G-F 20 Single Intraarticular Injection), Tarceva, Taxotere (Docetaxel for Injection), Technetium Tc 99m, Telavancin for Injection (Vibativ), Temsirolimus Injection (Torisel), Tenormin I.V. Injection (Atenolol Inj), Teriparatide (rDNA origin) Injection (Parfet), Testosterone Cypionate, Testosterone Enanthate, Testosterone Propionate, Tev-Tropin (Somatropin, rDNA Origin, for Injection), tgAAC94, Thallous Chloride, Theophylline, Thiotepa (Thiotepa Injection), Thymoglobulin (Anti-Thymocyte Globulin (Rabbit), Thyrogen (Thyrotropin Alfa for Injection), Ticarcillin Disodium and Clavulanate Potassium Gaiaxy (Timentin Injection), Tigan Injection (Trimethobenzamide Hydrochloride Injectable), Timentin Injection (Ticarcillin Disodium and Clavulanate Potassium Galaxy), TNKase, Tobramycin Injection (Tobramycin Injection), Tocilizumab Injection (Actemra), Torisel (Temsirolimus Injection), Totect (Dexrazoxane for Injection, Intravenous Infusion Only), Trastuzumab-DM1, Travasol (Amino Acids (Injection)), Treanda (Bendamustine Hydrochloride Injection), Trelstar (Triptorelin Pamoate for Injectable Suspension), Triamcinolone Acetonide, Triamcinolone Diacetate, Triamcinolone Hexacetonide Injectable Suspension (Aristospan Injection 20 mg), Triesence (Triamcinolone Acetonide Injectable Suspension), Trimethobenzamide Hydrochloride Injectable (Tigan Injection), Trimetrexate Glucuronate Inj (Neutrexin), Triptorelin Pamoate for Injectable Suspension (Trelstar), Twinject, Trivaris (Triamcinolone Acetonide Injectable Suspension), Trisenox (Arsenic Dioxide Injection), Twinrix, Typhoid Vi, Ultravist (Iopromide Injection), Urofollitropin for Injection (Metrodin), Urokinase Injection (Kinlytic), Ustekinumab (Stelara Injection), Ultralente (U), Valium (diazepam), Vaiproate Sodium Injection (Depacon), Valtropin (Somatropin Injection), Vancomycin Hydrochloride (Vancomycin Hydrochloride Injection), Vancomycin Hydrochloride Injection (Vancomycin Hydrochloride), Vaprisol (Conivaptan Hcl Injection), VAQTA, Vasovist (Gadofasveset Trisodium Injection for Intravenous Use), Vectibix (Panitumumab Injection for Intravenous Use), Venofer (Iron Sucrose Injection), Verteporfin Inj (Visudyne), Vibativ (Telavancin for Injection), Victoza (Liraglutide [rDNA] Injection), Vimpat (Iacosamide Tablet and Injection), Vinblastine Sulfate (Vinblastine Sulfate Injection), Vincasar PFS (Vincristine Sulfate Injection), Victoza, Vincristine Sulfate (Vincristine Sulfate Injection), Visudyne (Verteporfin Inj), Vitamin B-12, Vivitrol (Naltrexone XR lnj), Voluven (Hydroxyethyl Starch in Sodium Chloride Injection), Xeloda, Xenical (orlistat), Xeomin (Incobotulinumtoxin A for Injection), Xolair, Zantac Injection (Ranitidine Hydrochloride Injection), Zemplar Injection (Paricalcitol Injection Fliptop Vial), Zemuron (Rocuronium Bromide Injection), Zenapax (daclizumab), Zevalin, Zidovudine Injection (Retrovir IV), Zithromax Injection (Azithromycin), Zn-DTPA (Pentetate Zinc Trisodium Injection), Zofran Injection (Ondansetron Hydrochloride Injection), Zingo, Zoledronic Acid for Inj (Zometa), Zoledronic Acid Injection (Reclast), Zometa (Zoledronic Acid for Inj), Zosyn (Piperacillin and Tazobactam Injection), Zyprexa Relprevv (Olanzapine Extended Release Injectable Suspension) and a combination thereof.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A method of inspecting an unfilled, non-lubricated syringe, the method comprising:
    optically imaging a contact area between a syringe stopper positioned in a syringe barrel of an unfilled, non-lubricated syringe to form a contact image,
    wherein the contact image includes a seal line correlating to an engagement between a seal area of the syringe stopper and an inner diameter of the syringe barrel;
    analyzing the contact image to identify at least one discontinuity in the seal line based, at least in part on, one of:
        (i) a difference in contrast in the seal line;
        (ii) a difference in color in the seal line; or
        (iii) a combination thereof;
    determining that:
        (i) the syringe exceeds a defect criteria based upon the at least one discontinuity, or
        (ii) the syringe does not exceed the defect criteria based upon the at least one discontinuity;
    performing one of:
        (i) filling the barrel with a medicament when the syringe does not exceed the defect criteria; and
        (ii) indicating that the syringe is a defective syringe when the syringe exceeds the defect criteria.

2. The method of claim 1, wherein the at least one discontinuity includes a discontinuity extending across the seal line.

3. The method of claim 1, wherein optically imaging the contact area includes imaging the contact area with a line scan camera.

4. The method of claim 1, wherein optically imaging the contact area includes taking a plurality of images of the contact area about the circumference of the syringe.

5. The method of claim 1, wherein optically imaging the contact area includes obtaining image data as the syringe is rotated through at least one complete revolution.

6. The method of claim 1, wherein optically imaging the contact area includes generating a greyscale contact image.

7. The method of claim 1, wherein the syringe stopper has an indicating area adjacent to the seal area, and further wherein analyzing the continuity of the seal line includes comparing a color or intensity of the seal line and a color or intensity of the indicating area of the contact image.

8. The method of claim 1, wherein the contact image includes a plurality of seal lines correlating to engagement between a plurality of seal areas of the syringe stopper and the inner diameter of the syringe barrel.

9. A method of inspecting an unfilled, non-lubricated syringe, said method comprising:
    providing an unfilled, non-lubricated syringe comprising:
        a barrel having an inner diameter and an outer diameter;
        a syringe stopper inserted therein, the syringe stopper having a seal area;
    optically imaging a contact area between the syringe stopper and the inner diameter of the barrel to form a contact image, wherein the contact image includes a seal line correlating to contact between the seal area and the inner diameter of the barrel; and
    visually inspecting the contact image to identify at least one discontinuity in the seal line based, at least in part, on
    a discontinuous seal line;
    determining that:
        (i) the syringe exceeds a defect criteria based upon the at least one discontinuity, or
        (ii) the syringe does not exceed the defect criteria based upon the at least one discontinuity;
    performing one of:
        (i) filling the barrel with a medicament when the syringe does not exceed the defect criteria; and
        (ii) indicating that the syringe is a defective syringe when the syringe exceeds the defect criteria.

* * * * *